United States Patent
Meinel et al.

(10) Patent No.: US 9,526,803 B2
(45) Date of Patent: Dec. 27, 2016

(54) DIAGNOSTIC CHEWING GUM FOR PATHOGENS

(71) Applicant: Julius-Maximilians-Universitaet Wuerzburg, Wuerzburg (DE)

(72) Inventors: Lorenz Meinel, Wuerzburg (DE); Matthias Schnabelrauch, Jena (DE); Falko Schlottig, Fuellinsdorf (CH)

(73) Assignee: Julius-Maximilians-Universitaet Wuerzburg, Wuerzburg (DE)

( * ) Notice: Subject to any disclaimer, the term of this patent is extended or adjusted under 35 U.S.C. 154(b) by 0 days.

(21) Appl. No.: 14/383,682

(22) PCT Filed: Mar. 8, 2013

(86) PCT No.: PCT/EP2013/054715
§ 371 (c)(1),
(2) Date: Sep. 8, 2014

(87) PCT Pub. No.: WO2013/132058
PCT Pub. Date: Sep. 12, 2013

(65) Prior Publication Data
US 2015/0023879 A1    Jan. 22, 2015

(30) Foreign Application Priority Data

Mar. 8, 2012  (CH) ...................................... 0328/12

(51) Int. Cl.
*A23G 4/14* (2006.01)
*A61K 9/68* (2006.01)
(Continued)

(52) U.S. Cl.
CPC ............. *A61K 49/0004* (2013.01); *A23G 4/14* (2013.01); *A61K 9/0058* (2013.01); *A61K 49/00* (2013.01);
(Continued)

(58) Field of Classification Search
CPC ............. A23G 4/06; A23G 4/14; A23G 4/20; A61C 2201/002; A61K 6/002; A61K 9/0058; A61K 49/0004; A61K 2123/00; C12Q 1/04; C12Q 1/37; C12Q 2304/00; G01N 33/528; G01N 33/68; G01N 33/6893
See application file for complete search history.

(56) References Cited

U.S. PATENT DOCUMENTS 7,288,247 B2    10/2007   Wouters et al.
2001/0012636 A1*  8/2001  Azar et al. ..................... 436/163
(Continued)

FOREIGN PATENT DOCUMENTS

WO    WO 02/00920 A2    1/2002
WO    WO 2013/131993 A2 *  9/2013    .......... A61B 5/14546

OTHER PUBLICATIONS

UCLA Engineering, "A chewing gum diagnostic test for malaria", Los Angeles, CA (Jan. 1, 2010), URL: http://www.engineer.ucla.edu/newsroom/more-news/archive/2010/malaria-gum (retrieved May 20, 2013).

*Primary Examiner* — Jeffrey E Russel
(74) *Attorney, Agent, or Firm* — Chalin A. Smith; Smith Patent LLC

(57) ABSTRACT

Described herein is a diagnostic chewing gum for identifying the presence of pathogens detectable via the mouth, in particular pathogens residing in nasal, oropharyngeal, laryngeal, oesophageal, ocular and/or pulmonal tissue of a user, more particularly pathogens selected from among a virus, bacterium, protozoa, prion, fungus or a combination thereof. The inventive diagnostic chewing gum includes a base material or particles (3) embedded and/or attached to the base material and an element (1, 5-7), like e.g. a releasable flavor molecule, attached to the base material and/or the particles, for the generation of a change in the chewing gum
(Continued)

A

B

C directly detectable by the user, wherein the element (1, 5-7) generates the change upon direct or indirect contact with a marker (4) which is released by the pathogens, or, in case of a virus or prion, by the cellular structure hosting it.

27 Claims, 2 Drawing Sheets

(51) Int. Cl.
*A61K 49/00* (2006.01)
*G01N 33/68* (2006.01)
*G01N 33/52* (2006.01)
*C12Q 1/37* (2006.01)
*C12Q 1/04* (2006.01)

(52) U.S. Cl.
CPC ............ *A61K 49/0069* (2013.01); *C12Q 1/04* (2013.01); *C12Q 1/37* (2013.01); *G01N 33/528* (2013.01); *G01N 33/68* (2013.01); *G01N 33/6893* (2013.01); *A61C 2201/002* (2013.01); *C12Q 2304/00* (2013.01)

(56) References Cited

U.S. PATENT DOCUMENTS

| | | | |
|---|---|---|---|
| 2002/0034475 A1* | 3/2002 | Ribi | A23L 1/275 424/9.6 |
| 2011/0020240 A1* | 1/2011 | Cirillo et al. | 424/9.6 |

\* cited by examiner

DIAGNOSTIC CHEWING GUM FOR PATHOGENS

PRIORITY

This application corresponds to the national phase of International Application No. PCT/EP2013/054715, filed Mar. 8, 2013, which, in turn, claims priority to Swiss Patent Application No. 00328/12 filed Mar. 8, 2012, both of which are incorporated by reference herein in their entirety.

SEQUENCE LISTING

The instant application contains a Sequence Listing that has been submitted in ASCII format via EFS-Web and is hereby incorporated by reference in its entirety. Said ASCII copy, created on Sep. 8, 2014, is named LNK_154_SequenceListing.txt and is 27,912 bytes in size.

TECHNICAL FIELD

The present invention relates to device, in particular to a chewing gum, for the diagnosis of pathogens present in the mouth cavity and adjacent tissues.

PRIOR ART

Many pathogens colonize the mouth cavity and adjacent tissues, including the stomach, the lung, nasopharynx and others. Currently, the identification of these pathogens is complex and requires advanced instrumentation which is typically located in specialized centers in which a precise analysis is performed on biopsies or fluid samples collected from the patient. The systems include immunological or histological methods. Consequently, such systems are unable to be used for screening purposes within which an immediate answer must be provided.

SUMMARY OF THE INVENTION

It is therefore an object of the present invention to provide a new approach for the detection of pathogens in the mouth and adjacent tissues.

This and other objects are achieved by the claimed subject matter.

Specifically the present invention in particular relates to a diagnostic chewing gum for identifying the presence of pathogens detectable via the mouth, in particular present in the mouth cavity, respiratory ducts and entire lung, oesophagus, stomach, nasopharynx, oropharynx, or laryngopharyns of a user. In accordance with the present invention, this chewing gum comprises at least one base material or particles embedded and/or attached to said base material; at least one element, such as for example a molecule, for the generation of a change in the chewing gum directly detectable (i.e. without additional analytical tools or the like so basically by using at least one of the five senses, i.e. sight—ophthalmoception, hearing—audioception, taste—gustaoception, smell—olfacoception, and touch—tactioception, or a combination thereof) by the user. Said pathogen is selected from the group consisting of virus, bacterium, protozoa, prion, fungus or a combination thereof. Furthermore said element generates the change upon direct or indirect contact with a marker which is released by said pathogens, or, in case of a virus or prion, by the cellular structure hosting it. Generally speaking such a pathogen can e.g. be a protease from DNA or RNA of non-mammalian, or more precisely normally non-human origin. The invention does not relate to the detection of markers which are released by inflammatory tissue in response to bacterial mediators in dental applications, specifically not to proteases from DNA or RNA of mammalian, or more precisely normally human origin.

Surprisingly it was found that pathogenic biomarkers of pathogens present in the mouth cavity, respiratory ducts and entire lung, oesophagus, stomach, nasopharynx, oropharynx, or laryngopharynx are present in sufficient amounts in the mouth cavity to allow for such a pathogen detection system.

The proposed systems here allow for patient self-monitoring. The chain in this proposal is as follows: In response to pathogen presence, (i) a change for example in the form of a strong bitter taste is released by the system and (ii) this bitter taste can be reported by the patient. (iii) Based on this report, a diagnose can be made and (iv) can lead early on therapy if appropriate.

As pointed out above, detection of pathogens meets a true threat in today's advancement of oral and general health. The proposal is addressing this challenge by deploying the human senses, in particular for example the taste/gustatory system, for surveillance of connective tissue degradation and pathogen presence (see also FIG. 1). This radically new and easy to use diagnostic tool, identifies and stratifies subjects at risk for development of diseases caused by specific pathogens, opening a new window of opportunity for medical risk assessment and, therefore, possible intervention at an early stage. This early on detection allows pre-emptive, successful, non-complex and perhaps better tolerated treatment. The strategy followed here is disruptive in terms of shifting current point-of-care (PoC; i.e. the practitioner's office or clinic) diagnosis to self-monitoring, allowing consultation of one's medical practitioner in diseases stages which are clinically unapparent and within which relatively moderate therapeutic intervention suffice to prevent further destruction of the tissue and surrounding tissues and in contrast to more radical interventions necessary at later stages (see also FIG. 1).

A completely new diagnosing platform has thus been developed by means of gaining access to the advanced technological capabilities of several contributors.

According to a preferred embodiment of the present invention therefore, the marker inducing the change is a proteolytic enzyme released or, in case of a virus or a prion, upregulated, by pathogens, preferably by bacteria, viruses, protozoa or fungi, more preferably the following class, order, genera, family of species of herpes, varicella, parvovirus, papillomavirus, polyomavirus, adenovirus, hepadnavirus, variolavirus, picornavirus, aso- and caliciavirus, human cytomegalovirus, hepatitis-A-virus, hepatitis-C-virus, hepatitis-E-virus, togavirus, flavivirus, coronavirus, retrovirus, HIV, reovirus, orthomyxovirus, bunyavirusarenavirus, human rhinovirus, dengue virus, varicella-zoster virus, paramyxovirus, rubulavoris, morbillivirus, west nile virus, yellow fever virus, pneimovirus, non classified paramyxovirus, rhabdovirus, folovirus, viroids and prions, *staphylococcus, streptococcus* and *enterococcus, bacillus, listeria, erysipelothrix, garderella, corynebacterium, actinomyces, mycobacterium, nocardia, neisseria, acinetobacter* and *moraxella*, enterbacteriacea including *salmonella shigella, yersinia, E. coli* and *vibrio, aeromonas, plesiomonas, haemophilus, pasteurella, campyhlobacter, heliobacter, spirillum, pseudomonas, stenotropomonas, burkholderia, legionella, brucella, bordetella francisella*, bacteriodaceae including *trepponema, borrelia peptospira rickettsia, coxiella, orientia, ehrlichia, baronella afipia, chlamydia, myco-* plasma and histoplasma, coccidioides, blasomyces, paracoccidioides, candida, aspergillus, Cryptococcus, mucor, absidia, rhizopus, phaeohyphomycetes, hyalohyphomycetes, penicillium, pneumocystis, tyrpanoma, leishmania, giradia, trichomonas, entamoeba, naegleria, toxoplasma isspora, cyclospora, sarcocystis, cryptosporidium, plasmodium, babesia, microsporida, and balantidium.

The marker inducing the change in accordance with yet another preferred embodiment is most preferably a protease expressed by this pathogen, for example pathogen-specific proteases or a matrix metalloproteinase (MMP), in particular a matrix metalloproteinase-8 (MMP-8) or an activated matrix metalloproteinase-8 (aMMP-8).

TABLE 1

Selection of pathogens, associated proteases to which the sensitive system presented here within is responsive and examples of peptide sequences, which can be used to build the system, wherein the peptide sequences mentioned in the cited references are expressly included into the present disclosure (see FIG. 1).

| Pathogen | Protease | Literature, within which the protease sensitive sequence is mentioned |
|---|---|---|
| Kaposi's sarcoma-associated herpes virus (KSHV) (also called human herpes virus 8 (HHV-8)) | KSHV protease | A. Uenal et al., J. Virol., 71, 7030 (1997) |
|  | KSHV release site (R-site) | T. R. Pray et al., J. Mol. Biol., 289, 197 (1999) |
| herpes simplex virus type 1 (HSV-1) | herpes simplex virus type 1 protease (HSV-1 protease) | D. L. Hall and P. L. Darke, J. Biol. Chem., 270, 22697 (1995) |
|  |  | D. J. McGeoch et al., J. Gen. Virol., 69, 1531 (1988) |
|  |  | A. R. Welch et al., J. Virol., 65, 4091 (1991) |
|  |  | F. Liu and B. Roizman, J. Virol., 65, 206 (1991) |
|  |  | A. R. Welch et al., Proc. Natl. Acad. Sci. USA, 88, 10792 (1991) |
|  |  | D. R. O'Boyle et al., Virology, 236, 338 (1997) |
| Influenza and SARS | type II transmembrane serine proteases (TTSPs) TMPRSS2 and HAT | S. Bertram, PLoS One. 7, e35876. (2012) |
| Human papillomavirus 16 and 18 (HPV) | Matrix-metalloprotease MMP-2, MMP-9, MT1-MMP | L. B. Cardeal et al., PLoS One, 7, e33585. (2012) |
|  |  | M. Y Shiau et al., PLoS One.; 8. e54423 (2013) |
|  |  | S. T. Vilen et al., ScientificWorldJournal. 2013. 920595. (2013) |
| Human cytomegalovirus | human cytomegalovirus protease | P. R. Bonneau et al., Anal. Biochem., 255, 59 (1998) |
|  |  | P. R. Bonneau et al., Anal. Biochem., 255, 59 (1998) |
|  |  | S. R. LaPlante et al., J. Am. Chem. Soc., 121, 2974 (1999) |
|  | human CMV assemblin protease | B. P. Holskin et al., Anal. Biochem., 227, 148 (1995) |
|  |  | B. P. Holskin et al., Anal. Biochem., 227, 148 (1995) |
|  |  | R. Batra et al., Nat. Struct. Biol., 8, 810 (2001) |
| Human Rhinovirus-14 (HRV14) | Human Rhinovirus-14 (HRV14) Protease | M. G. Cordingley et al., J. Biol. Chem., 265, 9062 (1990) |
|  | human rhinovirus-14 2A protease | Q. M. Wang et al., Arch. Biochem. Biophys., 356, 12 (1998) |
|  | human rhinovirus-14 3C protease | Q. M. Wang et al., Anal. Biochem., 252, 238 (1997) |
|  | human rhinovirus 2A protease | Q. M. Wang et al., Arch. Biochem. Biophys., 356, 12 (1998) |
| Hepatitis A virus (HAV) | Hepatitis A virus protease | L. Qu, PLoS Pathog. 2011 7(9): e1002169 |
| Hepatitis C Virus (HCV) | NS3-4A protease | P. Hamill and F. Jean, Biochemistry, 44, 6586 (2005) |
|  | HCV NS3 protease | M. Taliani et al., Anal. Biochem., 240, 60 (1996) |
|  | NS3 protease | Y. Shimuzu et al., J. Virol., 70, 127 (1996) |
|  | serine NS3/4A protease | Y. Yang,. Proc. Natl. Acad. Sci. USA,. 24; 104 (2007) |
|  |  | E. Foy, Science. 16, 300 (2003) |

TABLE 1-continued

Selection of pathogens, associated proteases to which the sensitive system presented here within is responsive and examples of peptide sequences, which can be used to build the system, wherein the peptide sequences mentioned in the cited references are expressly included into the present disclosure (see FIG. 1).

| Pathogen | Protease | Literature, within which the protease sensitive sequence is mentioned |
|---|---|---|
| Dengue virus | Dengue virus protease | T J Chambers, Annu Rev Microbiol 1990, 44:649-688. |
|  |  | B. Falgout, J Virol 1991, 65 |
| Varicella-Zoster virus (VZV) | Varicella-Zoster virus protease | X. Qiu, Proc Natl Acad Sci USA. 1997,; 94(7) |
| Human immunodeficiency virus (HIV) | HIV protease | M. W. Pennington et al., Peptides 1992, Proceedings of the 22nd European Peptide Symposium, Interlaken, Switzerland, p. 936, C. H. Schneider and A. N. Eberle, eds., Escom, Leiden, (1993) |
|  | HIV-1 protease | E. D. Matayoshi et al., Science, 247, 954 (1990) |
|  |  | U. Nillroth et al., Antimicrob. Agents Chemother., 41, 2383 (1997) |
|  |  | L. Bannwarth et al., J. Med. Chem., 49, 4657 (2006) |
|  |  | M. W. Pennington et al., Peptides 1990, Proceedings of the 21st European Peptide Symposium, Platja d'Aro, Spain, p. 787, E. Giralt and D. Andreu, eds., Escom, Leiden, (1991) |
|  |  | A. D. Richards et al., J. Biol. Chem., 265, 7733 (1990) |
|  |  | L. H. Phylip et al., Biochem. Biophys. Res. Commun., 171, 439 (1990) |
|  |  | C. Paulus et al., J. Biol. Chem., 274, 21539 (1999) |
|  | HIV-2 Protease | K. C. Chou, ANALYTICAL BIOCHEMISTRY 233, 1-14 (1996) |
| West nile virus (WNV) | NS2B/3 protease | M. A. Brinton, Annu. Rev. Microbiol. 56, 371 (2002) |
| Yellow fever virus | Yellow fever virus NS2B/NS3 protease | M Y Kondo Biochem Biophys Res Commun. 2011; 407(4) |
| Plasmodia | Malaria Aspartyl Proteinase | Pennington et al., Innovation and Perspectives in Solid Phase Synthesis & Combinatorial Libraries, 5th International Symposium, London, p. 367, R. Epton, ed., Mayflower Scientific, (1998) |
|  |  | S. Jiang et al., Antimicrob. Agents Chemother., 45, 2577 (2001) |
|  |  | M. Stadler et al., J. Antibiot., 58, 775 (2005) |
| SARS | SARS main protease | C.-J. Kuo et al., Biochem. Biophys. Res. Commun., 318, 862 (2004) |
|  | SARS-coronavirus main protease Mpro | K. Anand et al., Science, 300, 1763 (2003) |
| Streptomyces albus | Streptomyces albus DD-carboxypeptidase | O. Dideberg, FEBS Lett.; 117, 1 (1980) |
| Candida albicans | Candida carboxyl (aspartic) proteinase | J. O. Capobianco, C. G. Lerner, R. C. Goldman, Analytical Biochemistry 204 (1): 96-102 (1992) |

The gustatory system principally has four primary taste submodalities recognizing sweet, sour, salty, and bitter. Maximal sensitivity is provided for bitter taste and bitter taste can be calibrated for control of inter-patient variability using methods outlined in the European Pharmacopoeia. Sweet taste is more difficult to calibrate among patients but used as a strategy as well in spite of potential challenges for individual calibration of sweet perception. The human tongue offers a fascinating range of sensitivity for tasting sweetness and bitterness, covering five orders of magnitude. Quinine sulfate (bitter) is sensed down to 0.0004 mM, rivaling even our most advanced analytical detectors available today. The artificial sweetener, saccharin, is recognized down to 0.02 mM by the average human. Within the context of this application it is important, that certain short peptides can be typically sensed down to 0.05 to 6 mM and this insight is deployed by designing peptide sequences for the system which result in bitter taste following cleavage. By this strategy, the coupling of a flavoring substance can be avoided as the cleaved peptide sequence itself mediates a bitter sensation recognized by the affected patient.

In conclusion, in particular a pathogen-specific protease sensitive system provides the necessary power to the medical practitioner for early detection and continuous surveillance of presence of pathogens. The system provides radically new, easy to use tools to the medical practitioner and patient for early on monitoring of pathogen presence with immediate relevance on patient health or for broad screening of humans as pathogenic carriers.

The proposed system aims at broad application, including sensing of nasal, pharyngeal, laryngeal, ocular and/or pulmonal alterations following the principle outlined here.

The system is thus radically shifting monitoring of pathogens from assessments involving complex machinery to self-monitoring using the human tongue or the human eye of the user as a sensitive detector. Instead of restricting the monitoring of the health status to visits at the medical practitioner, the approach supports frequent self-monitoring such that in case of positive signal, the subject can visit the medical practitioner's office to get a thorough diagnosis.

The system (see also FIG. 2) is the mode by which clinically unapparent diseased tissue becomes detected early on. The main innovation aspects are the following:

- The deployment of human taste sensing/gustatory system for monitoring of pathogens is radically new.
- Chewing gums with diagnostic features are known but not those which respond to an enzyme indicative for the presence of a pathogen.
- Selection of pathogen-specific protease sensitive systems from known sequences which provide the necessary performance to preferentially sense pathogen-specific protease at levels at which pathogenic flora is differentiated from non-pathogen flora.
- The correlation of pathogen presence with pathogen-specific protease presence as done here controls the information available in literature by data sets to provide a reliable basis for fine-tuning and adapting our system's sensitivity and selectivity to specific activities of a pathogen's lifecycle. Different proteases are activated at different time points of a pathogen's normal life cycle and, therefore systems are possible which are responsive not only to a pathogen but specifically to a certain activation status of the pathogen.
- Modern coupling techniques are deployed to decorate the plastic (spheric system) with the peptide sequences.

The coupled flavoring substances may reduce their potential for (bitter) taste once attached to the peptide sequence. This risk can be mitigated by selecting different coupling sites at the (bitter) tasting molecule, by selecting different (bitter) tasting molecules and by designing bitter tasting peptide sequences, which are known to induce a bitter taste. Correspondingly therefore in accordance with yet another preferred embodiment the element can on the one hand be a molecule or molecular assembly which, upon direct or indirect contact with the marker undergoes a color change perceivable by the naked eye of the user, and which is embedded or attached to the base material or to particles embedded and/or attached to said base material.

On the other hand the element can be a flavor molecule releasably, preferably releasably covalently, attached to the base material or to particles embedded and/or attached to said base material.

The flavor molecule can be (releasably) attached to the base material or to particles embedded and/or attached to said base material by means of a hydrogen bonding or by means of a molecular chain cleavable under direct or indirect contact with the marker. Release is for example possible by lysis of the molecular chain by the marker itself, it is however also possible by means of mechanisms such as agglomeration or attachment of the marker to the linker or another element close by, inducement of a conformational change or the like, corresponding reduction of the binding constant of the flavor molecule to the support and release of the molecule to generate the corresponding taste sensation.

The molecular chain can for example be a polypeptide chain or a sugar chain or a combination thereof. In case of a polypeptide chain, this is preferably constituted of 2-15, most preferably of 3-9 amino acids, and preferably the linker molecule is either directly or indirectly, via an anchoring element, attached to the base material or to particles embedded and/or attached to said base material.

Possible linker sequences to be used as molecular chain cleavable under direct or indirect contact with the marker for the attachment of e.g. a bitter flavor molecule such as quinine, caffeine, theobromine, naringin, sucralose or neotame are given by the following systems, where the cleavage site by the protease system is partly indicated by a slash:

The single-letter code for amino acids is used: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; Y, Tyr.

```
HAV (Hepatitis A virus):
                                            (SEQ ID NO: 1)
    DWSQ/GCSL (SEQ ID NO: 2)
    EISQ/SPTM (SEQ ID NO: 3)
    IREQSQ/HLDG (SEQ ID NO: 4)
    LSYQAQ/MEQL (SEQ ID NO: 5)
    FGGQ/VPLG
    L. Qu, PLoS Pathog. 2011 7 (9): e1002169

HVC (Hepatitis C Virus):
                                            (SEQ ID NO: 6)
    EVVTSTWV (SEQ ID NO: 7)
    MEECSQHL (SEQ ID NO: 8)
    TTPCSGSW (SEQ ID NO: 9)
    VVCCSMSY
    S. A. Shiryaev, PLoS One. 2012; 7(4): e35759.

(SEQ ID NO: 10)
    DLEVVTS
    S. S. Leinbach, Virology, 204, 1, 1994

(SEQ ID NO: 11)
    DLEVVT/STWV (SEQ ID NO: 12)
    DEMEEC/ASHL (SEQ ID NO: 13)
    DCSTPC/SGSW (SEQ ID NO: 14)
    ESVVCC/SMSY
    Y. Benureaua, Virology, 406, 2, 2010

HCV
                                           (SEQ ID NO: 15)
    NGVCWTVY/HGAGT (SEQ ID NO: 16)
    YTNVDN/DLVGWPAPQ (SEQ ID NO: 17)
    PISYLKGS/SGGPLL
```

-continued dengue virus type 1 DEN1

(SEQ ID NO: 18)
DGVFHTMWHVTRG (SEQ ID NO: 19)
WASVKKDLISYGGGW (SEQ ID NO: 20)
ALDFKPGTSGSPIV

DEN2

(SEQ ID NO: 21)
EGTFHTMWHVTRG (SEQ ID NO: 22)
WADVKKDLISYGGGW (SEQ ID NO: 23)
SLDFSPGTSGSPIV

DEN3

(SEQ ID NO: 24)
EGVFHTMWHVTRG (SEQ ID NO: 25)
WASVKKDLISYGGGW (SEQ ID NO: 26)
ALDFKPGTSGSPII

DEN4

(SEQ ID NO: 27)
EGVFHTMWHVTRG (SEQ ID NO: 28)
WADVRNDMISYGGGW (SEQ ID NO: 29)
TLDFKPGTSGSPII

Japanese encephalitis virus JE (SEQ ID NO: 30)
ENVFHTLWHTTRG (SEQ ID NO: 31)
WGSVKEDRIAYGGPW (SEQ ID NO: 32)
SLDYPRGTSGSPIL yellow fever virus YF (SEQ ID NO: 33)
GGVFHTMWHVTRG (SEQ ID NO: 34)
WASVKEDLVAYGGSW (SEQ ID NO: 35)
ALDYPSGTSGSPIV tick-borne encephalitis virus TBE (SEQ ID NO: 36)
KGVLHTMWHVTRG (SEQ ID NO: 37)
WADVREDWVCYGGAW (SEQ ID NO: 38)
PIDLVKGTSGSPIL
HCV, dengue virus type 1, 2, 3, 4 (DEN 1, 2, 3, 4, 5), A Grakoui, J Virol. 1993 May; 67 (5)

HIV:
HIV-1 Protease Cleavage Site Amino Acid Sequences:

(SEQ ID NO: 39)
VSQNY/PIVQN

-continued (SEQ ID NO: 40)
KARVL/AEAMS (SEQ ID NO: 41)
STAIM/MQKGN (SEQ ID NO: 42)
ERQAN/FLGKI (SEQ ID NO: 43)
RPGNF/LQSRP (SEQ ID NO: 44)
ERQAN/FLREN (SEQ ID NO: 45)
ENLAF/QQGEA (SEQ ID NO: 46)
TSFSF/PQITC (SEQ ID NO: 47)
CTLNF/PISPI (SEQ ID NO: 48)
GAETF/YVDGA (SEQ ID NO: 49)
IRKVL/FLDGI (SEQ ID NO: 50)
PDCAW/LEAQE T. De Oliveira T et al., 2003. *Journal of Virology* 77(17)
K. Ikuta et al., 2000. *Microbiol. Mol. Biol. Rev.* 64.
T. Jacks et al. 1998. *Nature* 331.
H. Krausslich et al., 1989. *Proc. Natl. Acad. Sci. USA* 86
R. Swanstrom and J. W. Wills. 1997. Cold Spring Harbor Laboratory, Cold Spring Harbor, N.Y.
S. Billich et al. 1988. *J. Biol. Chem.* 263

(SEQ ID NO: 142)
VSQNY/IVQN
M. Prabu-Jeyabalan et al., *Structure.* 2002 March; 10(3): 369-81.

| Sequence | Protein |
|---|---|
| TQIM/F E T F | Actin (SEQ ID NO: 51) |
| G Q V N/Y E E F | Calmodulin (SEQ ID NO: 52) |
| P F I F/E E E P | Pro-IL1-b (SEQ ID NO: 53) |
| S F N F/P Q I T | pol (SEQ ID NO: 54) |
| D T V L/E E M S | Autolysis (SEQ ID NO: 55) |
| A R V L/A E A M | gag (SEQ ID NO: 56) |
| A E E L/A E I F | Troponin C (SEQ ID NO: 57) |
| S L N L/R E T N | Vimentin (SEQ ID NO: 58) |
| A T I M/M Q R G | gag (SEQ ID NO: 59) |
| A E C F/R I F D | Troponin C (SEQ ID NO: 60) |
| D Q I L/I E I C | Autolysis (SEQ ID NO: 61) |
| D D L F/F E A D | Pro-IL1-b (SEQ ID NO: 62) |
| Y E E F/V Q M M | Calmodulin (SEQ ID NO: 63) |
| P I V G/A E T F | pol (SEQ ID NO: 64) |

| Sequence | Protein |
|---|---|
| T L N F/P I S P | pol (SEQ ID NO: 65) |
| R E A F/R V F D | Calmodulin (SEQ ID NO: 66) |
| A E T F/Y V D K | pol (SEQ ID NO: 67) |
| A Q T F/Y V N L | pol (SEQ ID NO: 68) |
| P T L L/T E A P | Actin (SEQ ID NO: 69) |
| S F I G/M E S A | Actin (SEQ ID NO: 70) |
| D A I N/T E F K | Vimentin (SEQ ID NO: 71) |
| Q I T L/W Q R P | Autolysis (SEQ ID NO: 72) |
| E L E F/P E G G | PE664E (SEQ ID NO: 73) |
| A N L/A E E A | PE40 (SEQ ID NO: 74) |
| S Q N Y/P I V Q | gag (SEQ ID NO: 75) |
| P G N F/L Q S R | gag (SEQ ID NO: 76) |
| K L V F/A E | AAPd (SEQ ID NO: 77) |
| G D A L/L E R N | PE40 (SEQ ID NO: 78) |
| K E L Y/P L T S | gag (SEQ ID NO: 79) |
| R Q A N/F L G K | gag (SEQ ID NO: 80) |
| S R S L/Y A S S | Vimentin (SEQ ID NO: 81) |
| A E A M/S Q V T | gag (SEQ ID NO: 82) |
| R K I L/F L D G | pol (SEQ ID NO: 83) |
| G S H L/V E A L | Insulin (SEQ ID NO: 84) |
| G G V Y/A T R S | Vimentin (SEQ ID NO: 85) |
| F R S G/V E T T | gag (SEQ ID NO: 86) |
| V E V A/E E E E | AAPd (SEQ ID NO: 87) |
| L P V N/G E F S | AAPd (SEQ ID NO: 88) |
| E T T A/L V C D | Actin (SEQ ID NO: 89) |
| H L V E/A L Y L | Insuline (SEQ ID NO: 90) |
| H Y G F/P T Y G | NF-kBf (SEQ ID NO: 91) |
| D S A D/A E E D | AAPd (SEQ ID NO: 92) |
| G W I L/G E H G | LDHg (SEQ ID NO: 93) |
| G W I L/A E H G | LDH (SEQ ID NO: 94) |
| A I Y/L A L Q | pol (SEQ ID NO: 95) |
| E K V Y/L A W V | pol (SEQ ID NO: 96) |
| V E I C/T E M E | pol (SEQ ID NO: 97) |
| T Q D F/W E V Q | pol (SEQ ID NO: 98) |
| L W M G/Y E L H | pol (SEQ ID NO: 99) |
| G D A Y/F S V P | pol (SEQ ID NO: 100) |
| E L E L/A E N R | pol (SEQ ID NO: 101) |
| S K D L/I A E I | pol (SEQ ID NO: 102) |
| L E V N/I V T D | pol (SEQ ID NO: 103) |
| G G N Y/P V Q H | gag (SEQ ID NO: 104) |
| A R L M/A E A L | gag (SEQ ID NO: 105) |
| P F A A/A Q Q R | gag (SEQ ID NO: 106) |
| P R N F/P V A Q | gag (SEQ ID NO: 107) |
| G L A A/P Q F S | gag/pol (SEQ ID NO: 108) |
| S L N L/P V A K | pol (SEQ ID NO: 109) |
| A E T F/Y T D G | pol (SEQ ID NO: 110) |
| R Q V L/F L E K | pol (SEQ ID NO: 111) |
| Q M I F K E E H G | Fibronectin k (SEQ ID NO: 112) |

Kuo-Chen Chou, *ANALYTICAL BIOCHEMISTRY* 233, 1-14 (1996)

HIV-2 Protease Cleavage Site Amino Acid Sequences:

| Sequence | Protein |
|---|---|
| S Q N Y/P I V Q | gag (SEQ ID NO: 113) |
| E E E L/A E C F | Troponin C (SEQ ID NO: 114) |
| T Q I M/F E T F | Actin (SEQ ID NO: 115) |
| G Q V N/Y E E F | Calmodulin (SEQ ID NO: 116) |
| G C N Y/P V Q H | gag (SEQ ID NO: 117) |
| P R N F/P V A Q | gag (SEQ ID NO: 118) |
| A E E L/A E I F | Troponin C (SEQ ID NO: 119) |
| P F A A/A Q Q R | gag (SEQ ID NO: 120) |
| R Q V L/F L E K | pol (SEQ ID NO: 121) |
| A T I M/M Q R G | gag (SEQ ID NO: 122) |
| S L N L/P V A K | pol (SEQ ID NO: 123) |
| A N L/A E E A | PE40 (SEQ ID NO: 124) |
| P T L L/T E A P | Actin (SEQ ID NO: 125) |
| S F I G/M E S A | Actin (SEQ ID NO: 126) |
| Y E E F/V Q M M | Calmodulin (SEQ ID NO: 127) |
| R H V M/T N L G | Calmodulin (SEQ ID NO: 128) |
| Y I S A/A E L R | Calmodulin (SEQ ID NO: 129) |
| G L A A/P Q F S | pol (SEQ ID NO: 130) |
| D G N G/T I D F | Calmodulin (SEQ ID NO: 131) |
| G D A L/L E R N | PE40 (SEQ ID NO: 132) |
| N P T E/A E L Q | Calmodulin (SEQ ID NO: 133) |
| R Q A G/F L G L | gag (SEQ ID NO: 134) |

Kuo-Chen Chou, *ANALYTICAL BIOCHEMISTRY* 233, 1-14 (1996)

Yellow fever:

SSRKRR/SHDVLTQ (SEQ ID NO: 135)

RIFGRR/SIPVNEQ (SEQ ID NO: 136)

VRGARR/SGDVLWQ (SEQ ID NO: 137)

SAAQRR/GRIGRNQ (SEQ ID NO: 138)

FAEGRR/GAAEVLQ (SEQ ID NO: 139)

KLAQRR/VFHGVAQ (SEQ ID NO: 140)

MKTGRR/GSANGKQ (SEQ ID NO: 141)

MY Kondo et al. Biochem Biophys Res Commun. 407 (4): 640-4 (2011)

Generally speaking, combinations of Tyr, Ile, Phe, Pro, Leu, Val (single-letter codes for potentially bitter amino acids were marked in red) can be used for the bitter part.

Ethylation or acetylation just ahead of the cleavage site can be used to reduce the bitterness sequences.

The flavor molecule upon release preferably triggers the gustatory system of the user, preferably by stimulating a sweet and/or bitter taste.

The change upon direct or in direct contact with the marker is, in accordance with yet another preferred embodiment, triggered when a minimum marker concentration in saliva of the user is reached, wherein preferably the marker is a pathogen protease and wherein the minimum marker concentration is in the range of 50-100 U or in the range of 500-700 U.

The element can be attached to a particle with a size in the range of 0.5-1000 μm, preferably in the range of 20-250 μm, wherein preferably the particle is based on a polymer or copolymer or a (co)polymer mixture or (co)polymer blend, preferably on a polymer or copolymer selected from the group consisting of polystyrene, poly(methylmethacrylate), also possible are polyethylene, polypropylene, poly(vinylchloride), polycarbonate, polyamide, polysulfone, poly (ethersulfone), polyether, poly(ether-ketone), poly(ether-ether-ketone), poly(tetrafluoroethylen), poly (vinylidenefluoride), polyester, poly(hydroxyalkanoate), polyurethane, polyimide, poly(ether-imide), poly(butadiene), poly(vinylbutyral), polyanhydride, poly(amino acid), poly(organosiloxane), cellulose, chitin or a mixture or blend thereof. The systems can form a three-dimensional matrix, e.g. due to cross-linking processes. The three-dimensional matrix can be based on carboxy groups, amino groups, thiol groups or combinations thereof. Preferably poly(methylmethacrylate) with a three-dimensional carboxy group matrix is used.

Preferably the element, or an interlinked anchoring element, is attached to the particle by means of conventional coupling techniques, preferably by amide formation using conventional peptide coupling methods, disulfide coupling, ester formation using common procedures like carbodiimide-activated esterifications, urethane, urea or isothiourea formation generated by reaction with diisocyanates or diisothiocyanates, ether formation by reaction with epoxy group containing molecules like diepoxides or activated haloalkyl derivatives, reaction with dialdehydes followed by reductive amination, Michael-type addition reaction as e. g. performed by reaction of an acrylated reaction partner with a thiol-modified one or by known Click Chemistry coupling protocols like the Cu(I)-promoted azide-alkyne [3+2] cycloaddition.

Nasal, oropharyngeal, laryngeal, ocular and/or pulmonal alterations due to pathogen presence normally are characterized by the activation of more or less specific pathogen-proteases, which are indicative for a risk of developing their associated disease. The origin of the pathogens can for example in particular be based on at least one of the following inflammatory states: rhinitis, sinusitis, pansinusitis, rhinosinusitis, pneumonitis, pharyngitis, laryngitis, conjunctivitis, uveitis, blepharitis, orbital cellulitis, frontal or paranasal or maxillary sinusitis, cold, influenza, influenzal infection, abscess in mouth or throat or nose or lung, TBC, pneumonia, mycosis in mouth or throat or nose or lung.

Furthermore the present invention relates to the use of a chewing gum as outlined above for the detection of pathogen presence detectable via the mouth, in particular in relation with nasal, oropharyngeal, laryngeal, oesophageal, ocular and/or pulmonal pathogen presence. Further embodiments of the invention are laid down in the dependent claims.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings, FIG. 1 schematically shows the diagnostic approach followed in this application for early diagnosis of risk factors for the development of infections, wherein the system (box 5) is sensing pathogen-specific protease regulation indicative for the presence of the pathogen; today pathogens are typically recognized once clinical signs appear (box 4) a stage at which the disease course may be irreversible and lasting complications may prevail or missing a disease state within which a patient is highly contaminous yet the outbreak of the disease with easy to identify symptoms has not commenced yet; today, assessments of viral, bacterial or fungal load typically involve complex biochemical tests, the results of which are only obtained with significant lag time; in contrast, the proposed systems are designed to allow on-demand, self-monitoring, so therefore the patient is providing continuous monitoring and based on this the medical practitioner can diagnose complications early on. Alternatively, such systems may be used to screen larger populations throughout threats (such as SARS, or bird flue) or for border control to screen immigrants for the presence of pathogens.

DESCRIPTION OF PREFERRED EMBODIMENTS

Figure 3:
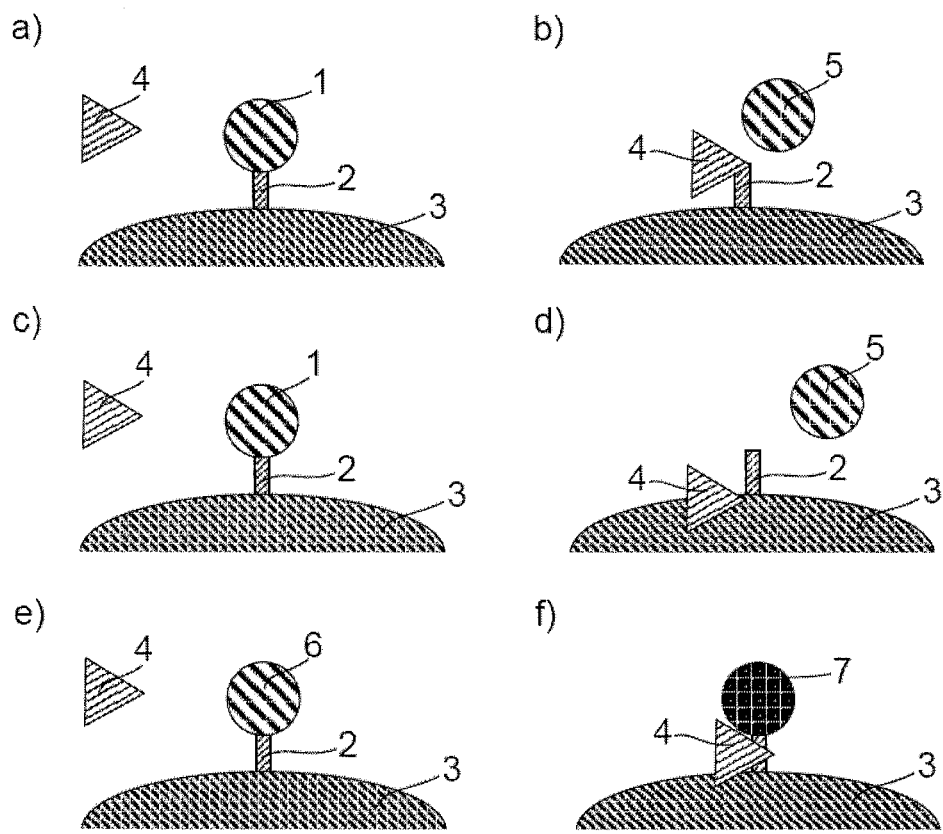
FIG. 3 shows different embodiments, wherein in a) and b) a first embodiment is shown, in which the linker sequence attached to a substrate or an anchor, to which initially (a) the flavoring substance is attached, is cleaved for the release of the flavoring substance (b), in c) and d) a second embodiment is shown, in which the linker sequence attached to a substrate or an anchor, to which initially (c) the flavoring substance is attached by a non-covalent bonding, for example a coordinative bonding, is conformationally changed such as to release the flavoring substance (d), and in e) and a third embodiment is shown, in which a substance attached via linker to a substrate (e) and showing a color change upon contact with the trigger molecule.

FIG. 3 shows different possibilities for attachment of releasable flavor substances 1 (a)-(d) or for the attachment of a colorant susceptible to change color upon interaction with MMP, in particular MMP-8, or another marker, present in saliva.

In the first embodiment as illustrated in FIG. 3 a, on a substrate 3, which can for example be a particle or the base material of the chewing gum, the flavoring substance molecule or complex 1 is attached via a linker element 2, normally a short and cleavable polypeptide chain. The flavoring substance molecule 1 may itself be a polypeptide or protein, and it may just be the extension of the linker element 2. Upon contact of the marker 4 present in saliva with the linker element 2, the latter is cleaved due to proteolytic interaction, releasing the flavoring substance into the free state 5, inducing the taste sensation (see FIG. 3b).

As illustrated in FIGS. 3c) and d), the interaction between the trigger/marker 4 present in saliva is not necessarily a direct interaction in the sense of a proteolytic interaction between the protease trigger and the linker element, it can also be an indirect interaction for example in the sense that the protease trigger attaches or forms a complex with the substrate in the vicinity of the linker element, induces some change, for example a change in the hydrogen bonding structure, and thereby releases the flavoring molecule or flavoring complex 5 into the surrounding saliva. In this case there is normally no chemical bond between the linker element 2 and the flavoring substance 1, however it is also possible that the protease trigger attaches and itself triggers a proteolytic system mounted on the substrate 3 or the linker element 2 leading to a proteolytic cleavage for the release of the flavoring substance. FIG. 3e) and f) show the situation where the protease trigger does not induce release of flavoring substance but a color change. To this end upon contact of the protease trigger 4 with the corresponding colorant substance 6, the latter is transformed into a second, differently colored state 7 leading to a visual signal perceptible to the user and indicative offer a sufficient level of protease trigger. It is not only possible that, as illustrated in FIG. 3e) and f), the color change takes place in a situation where the colorant 6 remains to be fixed to the chewing gum, it is also possible that the colorant 6 is released upon contact with the MMP trigger leading to a color change in saliva or in mouth tissue perceivable to the user.

EXPERIMENTAL SECTION

In a first step peptide sequences composed of (i) anchor coupled to (ii) sensitive peptide sequence coupled to (iii) flavoring substance using solid phase chemistry (FIG. 2), were synthesized by using a solid phase synthesis of pathogen-sensitive systems.

Three components of the system were synthesized (from C—N Terminus): (i) anchor coupled to (ii) sensitive peptide sequence coupled to (iii) flavoring substance.

30 systems with different protease sensitive protein sequences (as a platform from which sequences can be selected with best respective pathogen-protease selectivity and tailored sensitivity to pathogen-protease cleavage) were synthesized. Synthesis is performed using an automated solid phase peptide synthesis (SPPS) platform or peptides are obtained commercially. Synthesis (C to N-terminus) is following established protocols by coupling the carboxyl group of one amino acid to the amino group of another and by adequate use of protecting groups to avoid unintended reactions. Finally, the flavoring substance is attached as outlined below. The taste of the cleaved peptide sequence fragment coupled to the flavoring substance is tested by human volunteers and feedback from these tests helped to further modify the peptide sequence and flavoring substance for optimized bitter taste. Bitterness in oligopeptides is closely related to hydrophobicity. In fact and for screening purposes, one can proceed by assaying the Q value of peptides (a measure of the average hydrophobicity of a peptide, with Q>1,400 cal/mol being a threshold for possible bitter taste). Based on this approach, a selection of the following pathogen-protease cleavage products suggests bitterness or not: the first five sequences (sequences #1-5) of Table 2 of [NAGASE, H. & FIELDS, G. B. 1996; Human matrix metalloproteinase specificity studies using collagen sequence-based synthetic peptides. Biopolymers, 40, 399-416], show a Q* in cal/mol of approximately 1400-1700 and e.g. the fourth sequence in Table 2 shows bitter taste. If the cleaved peptide sequence is sufficiently bitter for reliable recognition, the coupling of the flavoring substance is sometimes not necessary in order to elicit a taste sensation in patients, as the peptide fragment is sufficiently mediating a taste itself.

Coupling of the Flavoring Substance

Figure 1:
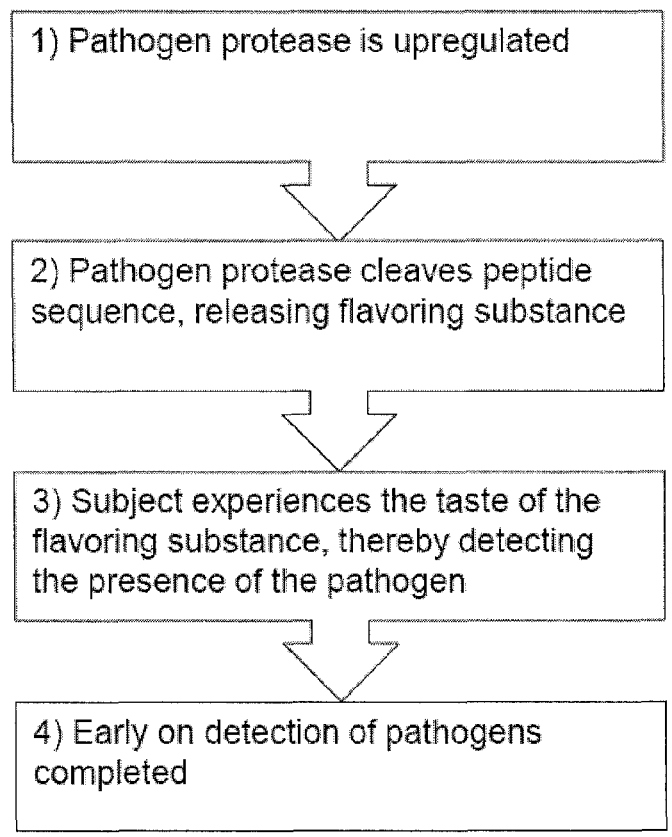
Figure 2:
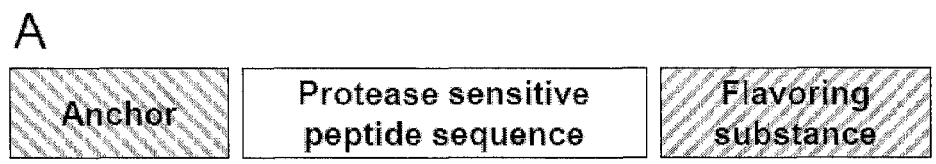
FIG. 2 shows in (A) how the functionality is linked to the pathogen's protease sensitive peptide sequence (center portion) located in between an anchor (left) and a flavoring substance (right); in (B) how the sequence is linked to particles or another surface, referred to as 'system' in this application; upon contact with pathogen protease at specific levels, the peptide sequence is cleaved and the off-coming flavoring substance triggers an intensive taste recognized by the patient; in (C) how the system is formulated into a chewing gum; during chewing, the self-monitoring is on for presence of pathogens being a prognostic factor for risk of disease development; the chewing gum is providing a full profile.
Figure 2:
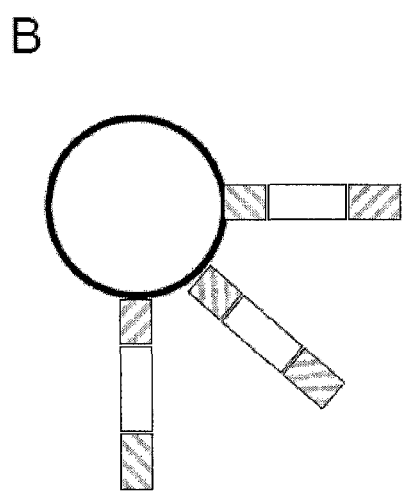
Figure 2:
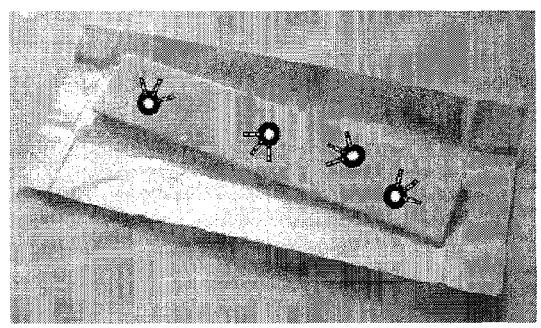

Coupling of quinine (bitter for gustatory detection and fluorescent for easy testing of cleavage, particularly when the spherical system is deployed) or aspartame, an artificial sweetener to the N-terminal end of the 'anchor-protease sensitive peptide' sequence can be performed while still on solid phase (see FIG. 2). Bifunctional linkers can be used to couple quinine to the N-terminal end of the anchor-protease sensitive protein sequence. To avoid rapid cleavage of the linker from quinine in vivo, hydrolytically or enzymatically less sensitive linkages can be installed. In a first approach, a diisocyanate linker like hexamethylene diisocyanate is treated with the free secondary OH-group of quinine forming an urethane bond followed by coupling the linker via its remaining isocyanate group to the N-terminal end of the peptide, forming an urea bond. A second approach consists in the reaction of the quinine double bond with a bis-epoxide (e. g. 1,4-butanediol diglycidyl ether) leading to an ether linked quinine which can be subsequently coupled to solid phase attached protein by N-alkylation. Aspartame, or if necessary a N-protected aspartame, can be coupled via its carboxyl group to the peptide N-terminus by conventional peptide synthesis. After coupling the flavoring molecules to the peptide, the formed conjugates can be cleaved from solid phase, purified and characterized using common analytical methods (FT-IR, NMR, MS). The strategy regarding the anchor is outlined below.

Formulation of a Spherical System in a Chewing Gum

To prepare peptide-flavoring substance conjugate-bearing spheres, poly(methylmethacrylate) (PMMA) carriers (particle diameter: 17 to 30 μm) with a three-dimensional carboxy group matrix are used. The conjugates synthesized as outlined above are immobilized to the PMMA spheres by conventional peptide formation protocols (e. g. by using water-soluble carbodiimides to activate the carboxyl groups of the PMMA matrix). In cases where conjugates with interfering functional groups are used the disulfide coupling method can be employed as described above.

For the coupling of peptides to build up the sensitive peptide sequence the following method was used:
Manual Coupling of Amino Acids:

After swelling the resin for 30 min in DMF and removing 1 mL 40% piperidine/DMF is added and incubated for 3 min. Then, after removing by vacuum filtration 1 mL 20% piperidine/DMF is added and incubated for 10 min. After removing the resin is washed 6 times with DMF (1 mL, 1 min each). The amino acid (5 eq) is dissolved in 410.90 µL 0.5 M HOBt in DMF and afterwards transferred to the N-terminal-deprotected peptidyl resin. 31.81 µL (8 eq) of DIC is added to the reaction mixture and gently shaken for 1 h. After removing the reaction mixture by vacuum filtration the resin is washed 6 times with DMF (1 mL, 1 min each) and 6 times with DCM (1 mL, 1 min each). After the cleavage of peptides by specific proteases the monoisotopic masses have to be checked with MALDI-MS. Preparative purification by high-pressure liquid chromatography (HPLC) is carried out with a Phenomenex C18 column (21.2-mm internal diameter, 250-mm length, 7-mm particle size) with eluent A (0.2% TFA in water) and eluent B (0.2% TFA in 1:4 water-acetonitrile). The peptides have to be purified with a gradient of 29 to 54% eluent B in 50 min.

For the coupling of the flavoring substance to the sensitive peptide sequence the following specific methods can be used:

Modification of Hydroxy Group-Containing Flavor Molecules with Anchor Groups

Example 1

1.5 mmol of the flavor molecule is dissolved in dichloromethane and consecutively 3 mmol of adipic acid, 3 mmol of N,N-dicyclohexylcarbodiimide and 3 mmol of 4-(N,N-dimethylamino)pyridine are added. The mixture is stirred for 24 hours at room temperature. Then, the reaction mixture is washed thoroughly with saturated $NaHCO_3$ solution, 2N HCl solution and water. The organic phase is isolated, dried over $MgSO_4$, and evaporated to dryness under vacuum. The obtained raw material is purified by flash chromatography using a silica gel column and chloroform/methanol as eluent.

Example 2

3 mmol dodecanedioic acid are stirred at room temperature with 3 mmol of 2,4,6-trichlorobenzoyl chloride and 10 mmol of triethylamine in toluene. After 3 hours stirring, 3 mmol of quinine and 3 mmol of 4-(N,N-dimethylamino) pyridine are added and the mixture is stirred for another 20 hours. The reaction mixture is washed thoroughly with saturated $NaHCO_3$ solution, and water, and the aqueous phase is washed twice with ethyl acetate. The organic phases are unified and dried over $MgSO_4$. After evaporation of the solvent under vacuum, the obtained raw material is purified by flash chromatography using a silica gel column and chloroform:methanol=3:1 as eluent. Yield: 47%, brown oil.

IR (ATR, $cm^{-1}$): 2923, 2852, 1738, 1623, 1590, 1505, 1476, 1433, 1357, 1305, 1229, 1157, 1090, 1033, 995, 914, 852, 829, 762, 719.

Example 3

Step 1: A mixture of 1 mmol of quinine, 1 mmol of 11-bromo-undecanoic acid, 1 mmol of N,N-dicyclohexylcarbodiimide and 1 mmol of 4-(N,N-dimethylamino)pyridine in dry dichloromethane are stirred for 24 h at room temperature. Then, the reaction mixture is washed thoroughly with saturated $NaHCO_3$ solution, 2N HCl solution and water. The organic phase is isolated, dried over $MgSO_4$, and evaporated to dryness under vacuum. The product is further purified by flash chromatography using a silica gel column and methanol as eluent. Yield: 20%, yellow oil. IR (ATR, $cm^{-1}$): 3323, 2924, 2852, 2119, 1738, 1695, 1619, 1571, 1509, 1452, 1357, 1310, 1223, 1167, 1086, 1029, 990, 914, 852, 833, 719, 647.

Step 2: 1 mmol of the flavor molecule containing a bromo group is dissolved in DMF and an excess of sodium azide (3 mmol) is added. The mixture is stirred for 20 h at room temperature. After addition of water the reaction mixture is extracted three times with ethyl acetate. The received raw product is further purified by flash chromatography using a silica gel column and chloroform:methanol=3:1 as eluent.

Example 4

2.5 mmol of the flavor molecule are dissolved in dichloromethane and 0.025 mmol of dibutyltin dilaurate followed by 5 mmol of hexamethylene diisocyanate dissolved in dichloromethane are added. The mixture is stirred for 24 hours at room temperature. After evaporation of the solvent the isocyanate-containing flavor molecule is used without further purification in the next step.

Example 5

2.5 mmol of the flavor molecule and 5 mmol of poly (ethylene glycol)-diepoxide (molecular weight: 2000 Da) are dissolved in DMSO (20 ml) followed by the addition of 5 mmol KOH. After stirring for 3 hours at room temperature water is added and the mixture is extracted with chloroform. The organic phase is dried over $MgSO_4$ and after evaporation of the solvent, the resulting product is used without further purification.

Modification of Peptides with Anchor Groups

Example 6

1 mmol of the peptide is dissolved in a dioxane/water mixture (1:1) and 2M NaOH is added until the pH reached 9-10. Under a nitrogen atmosphere, 1.1 mmol 3-butyn-1-yl-chloroformate is added and the mixture is allowed to stir for 18 hours. The product is lyophilised and purified by FCPC using an n-BuOH/$H_2O$ system. After purification the product is obtained as a white solid.

Coupling of the Carboxy Group-Containing Flavor Molecule with the Peptide

Example 7

A mixture of 1 mmol of the carboxy group-containing flavor molecule from example 1 or 2, 1 mmol of the peptide, 1 mmol of N,N-dicyclohexylcarbodiimide and 1 mmol of 4-(N,N-dimethylamino)pyridine in dry dichloromethane are stirred for 24 h at room temperature. Then, the reaction mixture is washed thoroughly with saturated $NaHCO_3$ solution, 2N HCl solution and water. The organic phase is isolated, dried over $MgSO_4$, and evaporated to dryness under vacuum. The product is further purified using preparative HPLC.

Example 8

0.5 mmol of the triple bond containing peptide from example 6 and 0.5 mmol of the azide group-containing flavor molecule from example 3 are dissolved in 20 ml of DMF. After addition of the catalyst copper-I-bromide/pentamethyldiethylenetriamine (0.05 mmol), the mixture is stirred for 24 hours at room temperature. After addition of water (150 ml), the mixture is extracted three times with chloroform. The unified chloroform extracts are washed with saturated $NaHCO_3$ solution, 2N HCl solution and water. The organic phase is dried over $MgSO_4$ and after evaporation of the solvent the peptide-coupled flavor molecule is obtained as a light yellow solid.

Example 9

1 mmol of isocyanate-terminated flavor molecule is dissolved in dichloromethane (10 ml) followed by the addition of 0.005 mmol dibutyltin dilaurate. After addition of 1 mmol of the peptide the mixture is stirred for 24 hours at room temperature. The reaction mixture is diluted by adding 10 ml of dichloromethane and washed with saturated $NaHCO_3$ solution, 2N HCl solution and water. The organic phase is dried over $MgSO_4$ and after evaporation of the solvent, the resulting raw product is purified using preparative HPLC.

Example 10

1 mmol of the epoxide-modified flavor molecule and 1 mmol of the peptide are dissolved in DMSO (20 ml). 2 mmol KOH are added and the mixture is stirred for 6 hours at room temperature. Water is added and the reaction mixture is extracted several times with chloroform. The organic phase is washed with saturated $NaHCO_3$ solution, 2N HCl solution and water. The chloroform extracts are dried over $MgSO_4$ and after evaporation of the solvent under vacuum, the remaining material is purified using preparative HPLC.

For the coupling of flavor molecule-modified peptide to polymer particles the following methods can be used:

Example 13

The amino group-containing polymer particles (100 mg) are suspended in dichloromethane and a solution of 1 mmol of the peptide in dry dichloromethane is added. After 5 min of stirring, 1 mmol of N,N-dicyclohexylcarbodiimide and 1 mmol of 4-(N,N-dimethylamino)pyridine dissolved in dichloromethane are added and the mixture is stirred 24 h at room temperature. The particles are isolated and washed twice with dichloromethane, ethanol, and water.

Example 14

The amino group-containing polymer particles (100 mg) and the flavor molecule-containing peptide (1 mmol) are suspended in phosphate buffer saline (10 mg/ml, pH=5-6). After 5 min, 1 mmol 1-(3-Dimethylaminopropyl)-3-ethyl-carbodiimide hydrochloride (EDC) and 0.6 mmol of N-hydroxysuccinimide are added and the mixture is stirred for 4 hours at room temperature. The polymer particles are isolated, washed with deionized water and purified by dialysis against deionized water for 36 hours at room temperature.

Suitable purification routines for the spheres have been established as well as analytical techniques to characterize them (particle size after immobilization, mechanical integrity, load capacity).

Development of a Spherical System Formulated in Chewing Gum

The chewing gum can be selected from sorbitol, mannitol or a combination of these sugars/polyols to result in strong bite strength (low load of spherical system), medium bite strength (caramel like in the beginning, medium load of spherical system), or smooth system (high load of spherical system). This starting material is a free floating powder, allowing easy mixture with other components, including spherical systems such as from above. The average powder particle size is about 200 to 250 µm or even 200 to 340 µm such that particle segregation can sometimes be problematic for spherical systems of diameters less than 20 µm. In cases in which segregation is a problem, one can prepare a pre-mix in Mannitol DC granulate and compact that premix. The powder mixture typically requires a lubricant for compression (e.g. 1.5% magnesium Stearate or 3% Mg-stearat: Talkum (1:1)). Compaction is done on a standard rotary tablet machine (possible advantageous Parameters: Pressing force: 7 KN, Pre-pressure: 2.2 KN, Cylinder height (compression): 2.8 mm, Cylinder height (pre-compression): 3.5 mm, Tablet diameter: 14 mm, Tablet height: 5 mm, Tablet weight: 1.15 gr). Turnover is up to 6,000 chewing gums per hour or at nearly any scale less, allowing pilot scale manufacturing for mitigating production risks for later production of the system in chewing gum. Miniaturized systems are used, allowing rapid formulation screens with lab scale experiments (mini-tablets/chewing gums) as are single-punch tablet machines one of which is equipped with appropriate pressure monitoring systems as a prerequisite for rationale design of tabletting conditions. A typical formulation is compressed from 86.5% or 86.95% Pharmagum® S, 0.5% or 0.05% spherical system, 3% magnesium stearate, 7% sorbitol and 3% sodium carbonate. As an alternative three different Health in Gum® by CAFOSA powder mixtures will be used. Typical formulations contain 92.7% Health in Gum®, 0.05% spherical system, 2.0% powder flavor, 2.0% encapsulated flavor, 1.5% lubricant, 1.0% silicon dioxide, 0.55% liquid flavor and 0.20% intensive sweeteners.

Stability tests were performed by exposing the spherical system/chewing gum formulation to different temperature and humidity profiles. The resulting chewing gums were chemically inert and not or only slightly hygroscopic and stable when stored. The formulations did not contain acid components such that re-agglomeration of the gum part while chewing was prevented. The resulting formulations were further characterized in terms of compression force, excipient optimization of the formulations, stability studies, compaction density by mercury porosimeter as well as measurements of hardness, water content and other standard pharmaceutical characterization tests.

Establishment of the System's Performance Against Proteases (Specificity and Sensitivity)

For these tests, an in-house machine can be engineered using a tool shop. By reference of the European Pharmacopeia (Pharm.Eur.) monograph for testing of chewing gums, the machine consists of two electronically controlled pistons transmitting twisting and pressing forces as occurring during chewing of a gum. A third vertical piston ('tongue') is holding the gum in place. The set-up is integrated into a temperature controlled chamber (40 mL volume) within which 20 mL of unspecified buffer or artificial saliva is placed. The buffer or saliva is spiked with respective protease as outlined below for testing performance (selectivity and specificity) of the spherical system formulated into a chewing gum. Fragments occurring in the buffer or artificial saliva are analyzed by HPLC equipped with a fluorescence detector (in case of quinine decoration, which is strongly fluorescent) or by LC-MS/MS to provide higher sensitivity.

In Vitro Testing of System Sensitivity to MMP Challenge

The system can be challenged to different proteases and 5 systems can be selected with optimized specificity and selectivity for protease cleavage.

Profile system cleavage as in FIG. 2B, D (coupled to spherical carrier or that coupled spherical carrier formulated into chewing gum) when exposed to Proteases, which can be purchased. Enzyme assays can be conducted to determine kcat/KM values (as substrate concentration is high, the enzyme is saturated and reaction kinetics are, therefore, controlled by kcat) and relative rate for sequence specificity (cross activity among different proteases tested). Cleavage can be assessed through conventional HPLC methods with UV-VIS detection and fluorescence detection where appropriate (fluorescence for e.g. quinine modified systems). Triple stage LC-MS/MS can be used for analysis and characterization of fragments. As fragments are below 1500 amu (m/z), the LC-MS/MS deployed at UWU is capable of robustly assessing these cleavage products with high sensitivity while concomitantly collecting structural data by means of tandem mass spectrometry (MS/MS) for enhanced identification and confirmation.

Evaluation of System Functionality/Chewing Gum in Patients, Performing Patient Acceptance Assessment/Gustatory Sensitivity of Flavoring Substances:

Patients with suspected inflammation or other pathogen presence can be used. After screening for their eligibility to participate in the study (inclusion/exclusion criteria) they are asked to sign the informed consent form (ICF). Clinical parameters are assessed. Patients with confirmed disease receive either the gustatory sensor in chewing gum or the corresponding "dummy" in a randomized order. Their gustatory response is recorded. Each patient is calibrated for his own correction factor as outlined below.

Sample size: At least 20 patients, (sequential study design with each patient being blinded and receiving the gustatory sensor in chewing gum or corresponding dummy with at least 30 minutes waiting time between administrations).

Methods: Patients with clinically confirmed elevated pathogen presence are treated with either the "gustatory sensor" in chewing gum (test group; provided in chewing gum as outlined above) and corresponding "dummy" (control group; as verum group with placebo chewing gum) using a predefined randomization list and at least 30 minutes waiting time between treatments. Individual gustatory response is normalized after calibration as outlined below.

Gustatory assessment, chewing of gustatory sensor in chewing gum: record patient gustatory experience (bitter taste/no specific taste) after calibration (individual correction factor is determined) of each patient as outlined below.

Taste Testing of System:

These studies are needed to evaluate the taste of the cleaved peptide sequences carrying the flavoring substance. For that, the truncated peptide sequence representing the "cleaved" part following protease-cleavage of the system and carrying the flavoring substance (see FIG. 2A) are tested as outlined below. Phase I is the calibration of each volunteers (determination of correction factor) and phase 2 is the exposure to the peptide fragment carrying the flavoring substance, for which bitterness values are collected as outlined below: The anticipated flavoring substances (bitter) used in this disclosure are not from a single chemical class (e.g. peptides vs. quinine). Bitter substances typically have a ring-bound carbonyl group, which may be part of a lactone ring system with ring opening typically leading to a loss of bitter taste. For assessment of bitter taste, the reciprocal value of the dilution of the bitter substance which is barely noticed as bitter, is taken. Therefore, the bitter value 10,000 means that 1 g of the subject tested and diluted in 10,000 mL water is barely recognized as bitter. The bitter value is determined as the average of 6 single measurements which is performed by 6 volunteers. As this is a biological testing assay, each person must be calibrated before the study commences with an individual correction factor being calculated for each volunteer after calibration has been finished. For that, quinine-HCl with a bitter value of 200,000 is used (dilute 0.1 g quinine-HCl R in 100 mL water R. 1 mL of that solution is taken and diluted to 100 mL with Water R=stock solution. Different volumes of that stock solution are diluted with water R to 10 mL=reference solution). If a volunteer barely tastes this reference solution as bitter, no correction factor is required. In all other cases, a correction factor is determined as follows: Each volunteer receives the same volume of diluted quinine-HCl. If the person is barely not sensing bitterness, the volunteer must keep the solution in his or her mouth for 30 seconds. Exactly 10 minutes must be waited before testing the person again with another dilution. The solution is held at room temperature and before the solution is tasted, the mouth is rinsed by the volunteer with water. During the entire procedure, it is not allowed to eat or smoke other than some unflavored white bread. The correction factor is calculated as of k=n/5 with n being the amount in milliliter of the stock solution barely tasted as bitter. Volunteers who cannot taste a reference solution composed of more than 5.8 mL stock solution diluted to 10 mL with water R are excluded from testing due to missing sensitivity. For testing of the flavoring substances/systems developed here within, the fragments generated after protease cleavage are manufactured and linked to the flavoring substance and these fragments are used for testing. For that, 10 mg of the fragment is dissolved in 1 mL of water R under agitation. After dissolution, this solution is diluted to 100 mL using water R (referred to as solution C1, which as a dilution factor of 100). 10 mL of that solution is diluted with water R to result in 100 mL of solution C2 (dilution factor 1,000) and so on. Starting as of C4, each volunteer determines ones individual bitter threshold level and barely tasted solution, respectively. This barely tasted solution is referred to as D. Using D, the following dilution set is prepared with the volumes always being filled to 10 mL using water R: 1.2, 1.5, 2.0, 3.0, 6.0, 8.0 mL. One determines the amount in mL of solution D, which is barely tasted as bitter. For each volunteer, the bitter value is calculated as follows: (Y*k)/(X*0.1), with Y being the individual dilution factor of Cn=D having been barely recognized as bitter, k being the correction factor as outlined above and X being the amount of mL of solution D, which has been recognized as bitter. The procedure is linked to an error of about 20-30%, which is respected during data interpretation.

LIST OF REFERENCE SIGNS 1 flavoring substance
2 linker element 3 substrate and/or anchor
4 pathogen specific and pathogen released protease trigger
5 released flavoring substance
6 colorant substance in first state
7 colorant substance in second coloured state

The invention claimed is:

1. A diagnostic chewing gum for identifying the presence of pathogens in nasal, oropharyngeal, oesophageal, laryngeal, ocular and/or pulmonal tissue or body liquids of a subject that are detectable via the mouth of said subject, said chewing gum comprising:
- a base material or particles (3) embedded and/or attached to said base material; and
- an element (1, 5-7) covalently attached to said base material and/or said particles for the generation of a change in the chewing gum that is directly detectable by the subject;
- wherein said pathogen is selected from the group consisting of virus, bacterium, fungus and combinations thereof;
- wherein the element (1, 5-7) generates the directly detectable change upon direct or indirect contact with a marker (4) that is released either by said pathogens, or, in case of a virus, by the cellular structure hosting it; and
- wherein said marker (4) inducing the directly detectable change is either (a) a proteolytic enzyme released by a bacterial or fungal pathogen, or by a cellular structure hosting a virus, or (b) a viral host, fungal or bacterial protease.

2. The chewing gum according to claim 1, wherein the element (1, 5-7) is a molecule or molecular assembly which, upon direct or indirect contact with the marker (4) undergoes a color change perceivable by the naked eye of the user.

3. The chewing gum according to claim 1, wherein the element (1, 5-7) is a flavor molecule (1, 5).

4. The chewing gum according to claim 3, wherein the flavor molecule (1) is covalently attached to the base material and/or said particles (3) by means of a molecular chain (2) cleavable under direct or indirect contact with the marker (4).

5. The chewing gum according to claim 4, wherein the cleavable molecular chain (2) is a polypeptide chain, that is either directly or indirectly, via an anchoring element, covalently attached to the base material (3) and/or to said particles (3).

6. The chewing gum according to claim 3, wherein the flavor molecule (1, 5) upon release triggers the gustatory system of the subject.

7. The chewing gum according to claim 3, wherein the flavor molecule (1, 5) is a polypeptide chain that is either directly or indirectly, via an anchoring element, covalently attached to the base material (3).

8. The chewing gum according to claim 1, wherein the change upon direct or indirect contact with the marker (4) is triggered when a minimum marker concentration in saliva of the subject is reached, wherein the marker (4) inducing the change is a viral host, fungal or bacterial protease selected from the group consisting of: KSHV-protease; HSV-protease; HAV-protease; HCV-protease; HIV-protease; human cytomegalovirus-protease; Yellow fever protease; CMV-protease; HRV14-protease; HRV2a-protease; Malaria aspartyl-protease; Sars protease; proteases of the S1, S2, S6, S8, S9, S33, S11, S12, S26, and S18 families; *streptomyces* trans-protease; *streptomyces* carboxypeptidase; signal peptidase I; Clp, C10, C11, C15, and C25 cysteine proteases; *porphyromonas gingivalis* cysteine proteases; sortase; metalloproteases of the thermolysin family (m4); Metalloproteases of the M9 family; Serralysin; M10 Proteases; proteases of the M12 family; bacterial metallo-exopeptidases; proteases of the M19, M20, M22, M23, and M26 families; tetanus neurotoxin; botulinum neurotoxin; anthrax toxin lethal factor; lysostaphin; aureolysin; and AAA proteases.

9. The chewing gum according to claim 1, wherein the change upon direct or indirect contact with the marker (4) is triggered when a minimum marker concentration in saliva of the subject is reached, wherein the marker (4) inducing the change is a viral host, fungal or bacterial protease selected from the group consisting of: KSHV-protease; HSV-protease; HAV-protease; HCV-protease; HIV-protease; human cytomegalovirus-protease; Yellow fever protease; CMV-protease; HRV14-protease; HRV2a-protease; Malaria aspartyl-protease; Sars protease; proteases of the S1, S2, S6, S8, S9, S33, S11, S12, S26, and S18 families; *streptomyces* trans-protease; *streptomyces* carboxypeptidase; signal peptidase I; Clp, C10, C11, C15, and C25 cysteine proteases; *porphyromonas gingivalis* cysteine proteases; sortase; metalloproteases of the thermolysin family (m4); Metalloproteases of the M9 family; Serralysin; M10 Proteases; proteases of the M12 family; bacterial metallo-exopeptidases; proteases of the M19, M20, M22, M23, and M26 families; tetanus neurotoxin; botulinum neurotoxin; anthrax toxin lethal factor; lysostaphin; aureolysin; and AAA proteases; and wherein the minimum marker concentration in saliva for the generation of a change in the chewing gum directly detectable by the subject is above 1 ng/ml.

10. The chewing gum according to claim 1, wherein the change upon direct or indirect contact with the marker (4) is triggered when a minimum marker concentration in saliva of the subject is reached, wherein the marker (4) inducing the change is a viral host, fungal or bacterial protease selected from the group consisting of: KSHV-protease; HSV-protease; HAV-protease; HCV-protease; HIV-protease; human cytomegalovirus-protease; Yellow fever protease; CMV-protease; HRV14-protease; HRV2a-protease; Malaria aspartyl-protease; Sars protease; proteases of the S1, S2, S6, S8, S9, S33, S11, S12, S26, and S18 families; *streptomyces* trans-protease; *streptomyces* carboxypeptidase; signal peptidase I; Clp, C10, C11, C15, and C25 cysteine proteases; *porphyromonas gingivalis* cysteine proteases; sortase; metalloproteases of the thermolysin family (m4); Metalloproteases of the M9 family; Serralysin; M10 Proteases; proteases of the M12 family; bacterial metallo-exopeptidases; proteases of the M19, M20, M22, M23, and M26 families; tetanus neurotoxin; botulinum neurotoxin; anthrax toxin lethal factor; lysostaphin; aureolysin; and AAA proteases; and wherein the minimum marker concentration in saliva for the generation of a change in the chewing gum directly detectable by the subject is in the range of 1-6000 ng/ml.

11. The chewing gum according to claim 1, wherein the element (1, 5-7) is covalently attached, either directly or via an anchoring element linked thereto, to a particle with a size in the range of 5-300 μm, wherein the particle is based on a polymer selected from the group consisting of: polystyrene, poly(methylmethacrylate), polyethylene, polypropylene, poly(vinylchloride), polycarbonate, polyamide, polysulfone, poly(ethersulfone), polyether, poly(ether-ketone), poly(ether-ether-ketone), poly(tetrafluoroethylene), poly(vinylidenefluoride), polyester, poly(hydroxyalkanoate), polyurethane, polyimide, poly(ether-imide), poly(butadiene), poly(vinylbutyral), polyanhydride, poly(amino acid), poly(organosiloxane), cellulose, chitin and mixtures thereof, and wherein the element (1, 5-7), and/or the anchoring element is covalently attached to the particle.

12. The chewing gum according to claim 1, wherein the element (1, 5-7) is covalently attached, either directly or via an anchoring element linked thereto, to the base material by means of a coupling technique selected from the group consisting of: amide formation using peptide coupling; disulfide coupling; ester formation; urethane formation; urea formation; isothiourea formation; ether formation; reaction with dialdehydes followed by reductive amination; Michael-type addition reaction; and Click Chemistry coupling protocols.

13. A method for the detection of a pathogen present in the nasal, oropharyngeal, oesophageal, laryngeal, ocular and/or pulmonal tissue or body liquids of a subject, said method comprising the step of administering the chewing gum of claim 1 to said subject.

14. The chewing gum according to claim 1, wherein the viral host, fungal or bacterial protease is selected from the group consisting of: KSHV-protease; HSV-protease; HAV-protease; HCV-protease; HIV-protease; human cytomegalovirus-protease; Yellow fever protease; CMV-protease; HRV14-protease; HRV2a-protease; Malaria aspartyl-protease; Sars protease; proteases of the S1, S2, S6, S8, S9, S33, S11, S12, S26, and S18 families; *streptomyces* trans-protease; *streptomyces* carboxypeptidase; signal peptidase I; Clp, C1, C10, C11, C15, and C25 cysteine proteases; *porphyromonas gingivalis* cysteine proteases; sortase; metalloproteases of the thermolysin family (m4); Metalloproteases of the M9 family; Serralysin; M10 Proteases; proteases of the M12 family; bacterial metallo-exopeptidases; proteases of the M19, M20, M22, M23, and M26 families; tetanus neurotoxin; botulinum neurotoxin; anthrax toxin lethal factor; lysostaphin; aureolysin; and AAA proteases.

15. The chewing gum according to claim 3, wherein the flavor molecule (1, 5) is covalently attached to the base material (3) or to the particles (3) embedded and/or attached to said base material.

16. The chewing gum according to claim 5, wherein the cleavable molecular chain (2) is a polypeptide chain that is 2-15 amino acids long.

17. The chewing gum according to claim 5, wherein the cleavable molecular chain (2) is a polypeptide chain that is 3-9 amino acids long.

18. The chewing gum according to claim 5, wherein the cleavable molecular chain (2) is a polypeptide chain having an amino acid sequence selected from the group consisting of SEQ ID NO:1 to SEQ ID NO:142, or a combination of a linker fraction thereof with a bitter amino acid selected from the group consisting of Tyr, Ile, Phe, Pro, Leu, and Val.

19. The chewing gum according to claim 6, wherein the flavor molecule (1, 5) triggers the gustatory system of the subject by stimulating a sweet and/or bitter taste.

20. The chewing gum according to claim 7, wherein the flavor molecule (1, 5) is a polypeptide chain that is 2-15 amino acids long.

21. The chewing gum according to claim 7, wherein the flavor molecule (1, 5) is a polypeptide chain that is 3-9 amino acids long.

22. The chewing gum according to claim 7, wherein the flavor molecule (1, 5) is a polypeptide chain having an amino acid sequence selected from the group consisting of SEQ ID NO:1 to SEQ ID NO:142, or a combination of a linker fraction thereof with a bitter amino acid selected from the group consisting of Tyr, Ile, Phe, Pro, Leu, and Val.

23. The chewing gum according to claim 1, wherein the change upon direct or indirect contact with the marker (4) is triggered when a minimum marker concentration in saliva of the subject is reached, wherein the marker (4) inducing the change is a viral host, fungal or bacterial protease selected from the group consisting of: KSHV-protease; HSV-protease; HAV-protease; HCV-protease; HIV-protease; human cytomegalovirus-protease; Yellow fever protease; CMV-protease; HRV14-protease; HRV2a-protease; Malaria aspartyl-protease; Sars protease; proteases of the S1, S2, S6, S8, S9, S33, S11, S12, S26, and S18 families; *streptomyces* trans-protease; *streptomyces* carboxypeptidase; signal peptidase I; Clp, C10, C11, C15, and C25 cysteine proteases; *porphyromonas gingivalis* cysteine proteases; sortase; metalloproteases of the thermolysin family (m4); Metalloproteases of the M9 family; Serralysin; M10 Proteases; proteases of the M12 family; bacterial metallo-exopeptidases; proteases of the M19, M20, M22, M23, and M26 families; tetanus neurotoxin; botulinum neurotoxin; anthrax toxin lethal factor; lysostaphin; aureolysin; and AAA proteases; and wherein the minimum marker concentration in saliva for the generation of a change in the chewing gum directly detectable by the subject is above 5 ng/ml.

24. The chewing gum according to claim 1, wherein the change upon direct or indirect contact with the marker (4) is triggered when a minimum marker concentration in saliva of the subject is reached, wherein the marker (4) inducing the change is a viral host, fungal or bacterial protease selected from the group consisting of: KSHV-protease; HSV-protease; HAV-protease; HCV-protease; HIV-protease; human cytomegalovirus-protease; Yellow fever protease; CMV-protease; HRV14-protease; HRV2a-protease; Malaria aspartyl-protease; Sars protease; proteases of the S1, S2, S6, S8, S9, S33, S11, S12, S26, and S18 families; *streptomyces* trans-protease; *streptomyces* carboxypeptidase; signal peptidase I; Clp, C10, C11, C15, and C25 cysteine proteases; *porphyromonas gingivalis* cysteine proteases; sortase; metalloproteases of the thermolysin family (m4); Metalloproteases of the M9 family; Serralysin; M10 Proteases; proteases of the M12 family; bacterial metallo-exopeptidases; proteases of the M19, M20, M22, M23, and M26 families; tetanus neurotoxin; botulinum neurotoxin; anthrax toxin lethal factor; lysostaphin; aureolysin; and AAA proteases; and wherein the minimum marker concentration in saliva for the generation of a change in the chewing gum directly detectable by the subject is above 8 ng/ml.

25. The chewing gum according to claim 1, wherein the change upon direct or indirect contact with the marker (4) is triggered when a minimum marker concentration in saliva of the subject is reached, wherein the marker (4) inducing the change is a viral host, fungal or bacterial protease selected from the group consisting of: KSHV-protease; HSV-protease; HAV-protease; HCV-protease; HIV-protease; human cytomegalovirus-protease; Yellow fever protease; CMV-protease; HRV14-protease; HRV2a-protease; Malaria aspartyl-protease; Sars protease; proteases of the S1, S2, S6, S8, S9, S33, S11, S12, S26, and S18 families; *streptomyces* trans-protease; *streptomyces* carboxypeptidase; signal peptidase I; Clp, C10, C11, C15, and C25 cysteine proteases; *porphyromonas gingivalis* cysteine proteases; sortase; metalloproteases of the thermolysin family (m4); Metalloproteases of the M9 family; Serralysin; M10 Proteases; proteases of the M12 family; bacterial metallo-exopeptidases; proteases of the M19, M20, M22, M23, and M26 families; tetanus neurotoxin; botulinum neurotoxin; anthrax toxin lethal factor; lysostaphin; aureolysin; and AAA proteases; and wherein the minimum marker concentration in saliva for the generation of a change in the chewing gum directly detectable by the subject is in the range of 5-4000 ng/ml.

26. The chewing gum according to claim 1, wherein the change upon direct or indirect contact with the marker (4) is triggered when a minimum marker concentration in saliva of the subject is reached, wherein the marker (4) inducing the change is a viral host, fungal or bacterial protease selected from the group consisting of: KSHV-protease; HSV-protease; HAV-protease; HCV-protease; HIV-protease; human cytomegalovirus-protease; Yellow fever protease; CMV-protease; HRV14-protease; HRV2a-protease; Malaria aspartyl-protease; Sars protease; proteases of the S1, S2, S6, S8, S9, S33, S11, S12, S26, and S18 families; *streptomyces* trans-protease; *streptomyces* carboxypeptidase; signal peptidase I; Clp, C10, C11, C15, and C25 cysteine proteases; *porphyromonas gingivalis* cysteine proteases; sortase; metalloproteases of the thermolysin family (m4); Metalloproteases of the M9 family; Serralysin; M10 Proteases; proteases of the M12 family; bacterial metallo-exopeptidases; proteases of the M19, M20, M22, M23, and M26 families; tetanus neurotoxin; botulinum neurotoxin; anthrax toxin lethal factor; lysostaphin; aureolysin; and AAA proteases; and wherein the minimum marker concentration in saliva for the generation of a change in the chewing gum directly detectable by the subject is in the range of 8-2000 ng/ml.

27. The chewing gum according to claim 1, wherein the element (1, 5-7) is covalently attached, either directly or via an anchoring element linked thereto, to a particle with a size in the range of 20-250 μm, wherein the particle is based on a polymer selected from the group consisting of: polystyrene, poly(methylmethacrylate), polyethylene, polypropylene, poly(vinylchloride), polycarbonate, polyamide, polysulfone, poly(ethersulfone), polyether, poly(ether-ketone), poly(ether-ether-ketone), poly(tetrafluoroethylene), poly(vinylidenefluoride), polyester, poly(hydroxyalkanoate), polyurethane, polyimide, poly(ether-imide), poly(butadiene), poly(vinylbutyral), polyanhydride, poly(amino acid), poly (organosiloxane), cellulose, chitin and mixtures thereof with a three-dimensional matrix due to cross-linking processes, wherein the three-dimensional matrix is based on carboxy groups, amino groups, thiol groups or combinations thereof and wherein the element (1, 5-7) or anchoring element is attached to the particle by means of a coupling technique selected from the group consisting of amide formation; disulfide coupling; ester formation via carbodiimide-activated esterification; urethane, urea and isothiourea formation generated by reaction with diisocyanates or diisothiocyanates; ether formation by reaction with epoxy group containing molecules; reaction with dialdehydes followed by reductive amination; Michael-type addition reaction as performed by reaction of an acrylated reaction partner with a thiol-modified one; Click Chemistry coupling protocols; and Cu(I)-promoted azide-alkyne [3+2] cycloaddition.

\* \* \* \* \*

SEQUENCE LISTING

<160> NUMBER OF SEQ ID NOS: 142

<210> SEQ ID NO 1
<211> LENGTH: 8
<212> TYPE: PRT
<213> ORGANISM: Artificial Sequence
<220> FEATURE:
<223> OTHER INFORMATION: peptide sequence

<400> SEQUENCE: 1

Asp Trp Ser Gln Gly Cys Ser Leu
1               5

<210> SEQ ID NO 2
<211> LENGTH: 8
<212> TYPE: PRT
<213> ORGANISM: Artificial Sequence
<220> FEATURE:
<223> OTHER INFORMATION: peptide sequence

<400> SEQUENCE: 2

Glu Ile Ser Gln Ser Pro Thr Met
1               5

<210> SEQ ID NO 3
<211> LENGTH: 10
<212> TYPE: PRT
<213> ORGANISM: Artificial Sequence
<220> FEATURE:
<223> OTHER INFORMATION: peptide sequence

<400> SEQUENCE: 3

Ile Arg Glu Gln Ser Gln His Leu Asp Gly
1               5                   10

<210> SEQ ID NO 4
<211> LENGTH: 10
<212> TYPE: PRT
<213> ORGANISM: Artificial Sequence
<220> FEATURE:
<223> OTHER INFORMATION: peptide sequence

<400> SEQUENCE: 4

Leu Ser Tyr Gln Ala Gln Met Glu Gln Leu
1               5                   10

<210> SEQ ID NO 5
<211> LENGTH: 8
<212> TYPE: PRT
<213> ORGANISM: Artificial Sequence
<220> FEATURE:
<223> OTHER INFORMATION: peptide sequence

<400> SEQUENCE: 5

Phe Gly Gly Gln Val Pro Leu Gly
1               5

<210> SEQ ID NO 6
<211> LENGTH: 8
<212> TYPE: PRT
<213> ORGANISM: Artificial Sequence
<220> FEATURE:
<223> OTHER INFORMATION: peptide sequence

<400> SEQUENCE: 6

Glu Val Val Thr Ser Thr Trp Val
1               5

```
<210> SEQ ID NO 7
<211> LENGTH: 8
<212> TYPE: PRT
<213> ORGANISM: Artificial Sequence
<220> FEATURE:
<223> OTHER INFORMATION: peptide sequence

<400> SEQUENCE: 7

Met Glu Glu Cys Ser Gln His Leu
1               5

<210> SEQ ID NO 8
<211> LENGTH: 8
<212> TYPE: PRT
<213> ORGANISM: Artificial Sequence
<220> FEATURE:
<223> OTHER INFORMATION: peptide sequence

<400> SEQUENCE: 8

Thr Thr Pro Cys Ser Gly Ser Trp
1               5

<210> SEQ ID NO 9
<211> LENGTH: 8
<212> TYPE: PRT
<213> ORGANISM: Artificial Sequence
<220> FEATURE:
<223> OTHER INFORMATION: peptide sequence

<400> SEQUENCE: 9

Val Val Cys Cys Ser Met Ser Tyr
1               5

<210> SEQ ID NO 10
<211> LENGTH: 7
<212> TYPE: PRT
<213> ORGANISM: Artificial Sequence
<220> FEATURE:
<223> OTHER INFORMATION: peptide sequence

<400> SEQUENCE: 10

Asp Leu Glu Val Val Thr Ser
1               5

<210> SEQ ID NO 11
<211> LENGTH: 10
<212> TYPE: PRT
<213> ORGANISM: Artificial Sequence
<220> FEATURE:
<223> OTHER INFORMATION: peptide sequence

<400> SEQUENCE: 11

Asp Leu Glu Val Val Thr Ser Thr Trp Val
1               5                   10

<210> SEQ ID NO 12
<211> LENGTH: 10
<212> TYPE: PRT
<213> ORGANISM: Artificial Sequence
<220> FEATURE:
<223> OTHER INFORMATION: peptide sequence

<400> SEQUENCE: 12

Asp Glu Met Glu Glu Cys Ala Ser His Leu
1               5                   10
```

```
<210> SEQ ID NO 13
<211> LENGTH: 10
<212> TYPE: PRT
<213> ORGANISM: Artificial Sequence
<220> FEATURE:
<223> OTHER INFORMATION: peptide sequence

<400> SEQUENCE: 13

Asp Cys Ser Thr Pro Cys Ser Gly Ser Trp
1               5                   10

<210> SEQ ID NO 14
<211> LENGTH: 10
<212> TYPE: PRT
<213> ORGANISM: Artificial Sequence
<220> FEATURE:
<223> OTHER INFORMATION: peptide sequence

<400> SEQUENCE: 14

Glu Ser Val Val Cys Cys Ser Met Ser Tyr
1               5                   10

<210> SEQ ID NO 15
<211> LENGTH: 13
<212> TYPE: PRT
<213> ORGANISM: Artificial Sequence
<220> FEATURE:
<223> OTHER INFORMATION: peptide sequence

<400> SEQUENCE: 15

Asn Gly Val Cys Trp Thr Val Tyr His Gly Ala Gly Thr
1               5                   10

<210> SEQ ID NO 16
<211> LENGTH: 15
<212> TYPE: PRT
<213> ORGANISM: Artificial Sequence
<220> FEATURE:
<223> OTHER INFORMATION: peptide sequence

<400> SEQUENCE: 16

Tyr Thr Asn Val Asp Asn Asp Leu Val Gly Trp Pro Ala Pro Gln
1               5                   10                  15

<210> SEQ ID NO 17
<211> LENGTH: 14
<212> TYPE: PRT
<213> ORGANISM: Artificial Sequence
<220> FEATURE:
<223> OTHER INFORMATION: peptide sequence

<400> SEQUENCE: 17

Pro Ile Ser Tyr Leu Lys Gly Ser Ser Gly Gly Pro Leu Leu
1               5                   10

<210> SEQ ID NO 18
<211> LENGTH: 13
<212> TYPE: PRT
<213> ORGANISM: Artificial Sequence
<220> FEATURE:
<223> OTHER INFORMATION: peptide sequence

<400> SEQUENCE: 18

Asp Gly Val Phe His Thr Met Trp His Val Thr Arg Gly
1               5                   10
```

```
<210> SEQ ID NO 19
<211> LENGTH: 15
<212> TYPE: PRT
<213> ORGANISM: Artificial Sequence
<220> FEATURE:
<223> OTHER INFORMATION: peptide sequence

<400> SEQUENCE: 19

Trp Ala Ser Val Lys Lys Asp Leu Ile Ser Tyr Gly Gly Gly Trp
1               5                   10                  15

<210> SEQ ID NO 20
<211> LENGTH: 14
<212> TYPE: PRT
<213> ORGANISM: Artificial Sequence
<220> FEATURE:
<223> OTHER INFORMATION: peptide sequence

<400> SEQUENCE: 20

Ala Leu Asp Phe Lys Pro Gly Thr Ser Gly Ser Pro Ile Val
1               5                   10

<210> SEQ ID NO 21
<211> LENGTH: 13
<212> TYPE: PRT
<213> ORGANISM: Artificial Sequence
<220> FEATURE:
<223> OTHER INFORMATION: peptide sequence

<400> SEQUENCE: 21

Glu Gly Thr Phe His Thr Met Trp His Val Thr Arg Gly
1               5                   10

<210> SEQ ID NO 22
<211> LENGTH: 15
<212> TYPE: PRT
<213> ORGANISM: Artificial Sequence
<220> FEATURE:
<223> OTHER INFORMATION: peptide sequence

<400> SEQUENCE: 22

Trp Ala Asp Val Lys Lys Asp Leu Ile Ser Tyr Gly Gly Gly Trp
1               5                   10                  15

<210> SEQ ID NO 23
<211> LENGTH: 14
<212> TYPE: PRT
<213> ORGANISM: Artificial Sequence
<220> FEATURE:
<223> OTHER INFORMATION: peptide sequence

<400> SEQUENCE: 23

Ser Leu Asp Phe Ser Pro Gly Thr Ser Gly Ser Pro Ile Val
1               5                   10

<210> SEQ ID NO 24
<211> LENGTH: 13
<212> TYPE: PRT
<213> ORGANISM: Artificial Sequence
<220> FEATURE:
<223> OTHER INFORMATION: peptide sequence

<400> SEQUENCE: 24

Glu Gly Val Phe His Thr Met Trp His Val Thr Arg Gly
1               5                   10

<210> SEQ ID NO 25
```

```
<211> LENGTH: 15
<212> TYPE: PRT
<213> ORGANISM: Artificial Sequence
<220> FEATURE:
<223> OTHER INFORMATION: peptide sequence

<400> SEQUENCE: 25

Trp Ala Ser Val Lys Lys Asp Leu Ile Ser Tyr Gly Gly Gly Trp
1               5                   10                  15

<210> SEQ ID NO 26
<211> LENGTH: 14
<212> TYPE: PRT
<213> ORGANISM: Artificial Sequence
<220> FEATURE:
<223> OTHER INFORMATION: peptide sequence

<400> SEQUENCE: 26

Ala Leu Asp Phe Lys Pro Gly Thr Ser Gly Ser Pro Ile Ile
1               5                   10

<210> SEQ ID NO 27
<211> LENGTH: 13
<212> TYPE: PRT
<213> ORGANISM: Artificial Sequence
<220> FEATURE:
<223> OTHER INFORMATION: peptide sequence

<400> SEQUENCE: 27

Glu Gly Val Phe His Thr Met Trp His Val Thr Arg Gly
1               5                   10

<210> SEQ ID NO 28
<211> LENGTH: 15
<212> TYPE: PRT
<213> ORGANISM: Artificial Sequence
<220> FEATURE:
<223> OTHER INFORMATION: peptide sequence

<400> SEQUENCE: 28

Trp Ala Asp Val Arg Asn Asp Met Ile Ser Tyr Gly Gly Gly Trp
1               5                   10                  15

<210> SEQ ID NO 29
<211> LENGTH: 14
<212> TYPE: PRT
<213> ORGANISM: Artificial Sequence
<220> FEATURE:
<223> OTHER INFORMATION: peptide sequence

<400> SEQUENCE: 29

Thr Leu Asp Phe Lys Pro Gly Thr Ser Gly Ser Pro Ile Ile
1               5                   10

<210> SEQ ID NO 30
<211> LENGTH: 13
<212> TYPE: PRT
<213> ORGANISM: Artificial Sequence
<220> FEATURE:
<223> OTHER INFORMATION: peptide sequence

<400> SEQUENCE: 30

Glu Asn Val Phe His Thr Leu Trp His Thr Thr Arg Gly
1               5                   10

<210> SEQ ID NO 31
<211> LENGTH: 15
```

```
<212> TYPE: PRT
<213> ORGANISM: Artificial Sequence
<220> FEATURE:
<223> OTHER INFORMATION: peptide sequence

<400> SEQUENCE: 31

Trp Gly Ser Val Lys Glu Asp Arg Ile Ala Tyr Gly Gly Pro Trp
1               5                   10                  15

<210> SEQ ID NO 32
<211> LENGTH: 14
<212> TYPE: PRT
<213> ORGANISM: Artificial Sequence
<220> FEATURE:
<223> OTHER INFORMATION: peptide sequence

<400> SEQUENCE: 32

Ser Leu Asp Tyr Pro Arg Gly Thr Ser Gly Ser Pro Ile Leu
1               5                   10

<210> SEQ ID NO 33
<211> LENGTH: 13
<212> TYPE: PRT
<213> ORGANISM: Artificial Sequence
<220> FEATURE:
<223> OTHER INFORMATION: peptide sequence

<400> SEQUENCE: 33

Gly Gly Val Phe His Thr Met Trp His Val Thr Arg Gly
1               5                   10

<210> SEQ ID NO 34
<211> LENGTH: 15
<212> TYPE: PRT
<213> ORGANISM: Artificial Sequence
<220> FEATURE:
<223> OTHER INFORMATION: peptide sequence

<400> SEQUENCE: 34

Trp Ala Ser Val Lys Glu Asp Leu Val Ala Tyr Gly Gly Ser Trp
1               5                   10                  15

<210> SEQ ID NO 35
<211> LENGTH: 14
<212> TYPE: PRT
<213> ORGANISM: Artificial Sequence
<220> FEATURE:
<223> OTHER INFORMATION: peptide sequence

<400> SEQUENCE: 35

Ala Leu Asp Tyr Pro Ser Gly Thr Ser Gly Ser Pro Ile Val
1               5                   10

<210> SEQ ID NO 36
<211> LENGTH: 13
<212> TYPE: PRT
<213> ORGANISM: Artificial Sequence
<220> FEATURE:
<223> OTHER INFORMATION: peptide sequence

<400> SEQUENCE: 36

Lys Gly Val Leu His Thr Met Trp His Val Thr Arg Gly
1               5                   10

<210> SEQ ID NO 37
<211> LENGTH: 15
<212> TYPE: PRT
```

```
<213> ORGANISM: Artificial Sequence
<220> FEATURE:
<223> OTHER INFORMATION: peptide sequence

<400> SEQUENCE: 37

Trp Ala Asp Val Arg Glu Asp Trp Val Cys Tyr Gly Gly Ala Trp
1               5                   10                  15

<210> SEQ ID NO 38
<211> LENGTH: 14
<212> TYPE: PRT
<213> ORGANISM: Artificial Sequence
<220> FEATURE:
<223> OTHER INFORMATION: peptide sequence

<400> SEQUENCE: 38

Pro Ile Asp Leu Val Lys Gly Thr Ser Gly Ser Pro Ile Leu
1               5                   10

<210> SEQ ID NO 39
<211> LENGTH: 10
<212> TYPE: PRT
<213> ORGANISM: Artificial Sequence
<220> FEATURE:
<223> OTHER INFORMATION: peptide sequence

<400> SEQUENCE: 39

Val Ser Gln Asn Tyr Pro Ile Val Gln Asn
1               5                   10

<210> SEQ ID NO 40
<211> LENGTH: 10
<212> TYPE: PRT
<213> ORGANISM: Artificial Sequence
<220> FEATURE:
<223> OTHER INFORMATION: peptide sequence

<400> SEQUENCE: 40

Lys Ala Arg Val Leu Ala Glu Ala Met Ser
1               5                   10

<210> SEQ ID NO 41
<211> LENGTH: 10
<212> TYPE: PRT
<213> ORGANISM: Artificial Sequence
<220> FEATURE:
<223> OTHER INFORMATION: peptide sequence

<400> SEQUENCE: 41

Ser Thr Ala Ile Met Met Gln Lys Gly Asn
1               5                   10

<210> SEQ ID NO 42
<211> LENGTH: 10
<212> TYPE: PRT
<213> ORGANISM: Artificial Sequence
<220> FEATURE:
<223> OTHER INFORMATION: peptide sequence

<400> SEQUENCE: 42

Glu Arg Gln Ala Asn Phe Leu Gly Lys Ile
1               5                   10

<210> SEQ ID NO 43
<211> LENGTH: 10
<212> TYPE: PRT
<213> ORGANISM: Artificial Sequence
```

<220> FEATURE:
<223> OTHER INFORMATION: peptide sequence

<400> SEQUENCE: 43

Arg Pro Gly Asn Phe Leu Gln Ser Arg Pro
1               5                   10

<210> SEQ ID NO 44
<211> LENGTH: 10
<212> TYPE: PRT
<213> ORGANISM: Artificial Sequence
<220> FEATURE:
<223> OTHER INFORMATION: peptide sequence

<400> SEQUENCE: 44

Glu Arg Gln Ala Asn Phe Leu Arg Glu Asn
1               5                   10

<210> SEQ ID NO 45
<211> LENGTH: 10
<212> TYPE: PRT
<213> ORGANISM: Artificial Sequence
<220> FEATURE:
<223> OTHER INFORMATION: peptide sequence

<400> SEQUENCE: 45

Glu Asn Leu Ala Phe Gln Gln Gly Glu Ala
1               5                   10

<210> SEQ ID NO 46
<211> LENGTH: 10
<212> TYPE: PRT
<213> ORGANISM: Artificial Sequence
<220> FEATURE:
<223> OTHER INFORMATION: peptide sequence

<400> SEQUENCE: 46

Thr Ser Phe Ser Phe Pro Gln Ile Thr Cys
1               5                   10

<210> SEQ ID NO 47
<211> LENGTH: 10
<212> TYPE: PRT
<213> ORGANISM: Artificial Sequence
<220> FEATURE:
<223> OTHER INFORMATION: peptide sequence

<400> SEQUENCE: 47

Cys Thr Leu Asn Phe Pro Ile Ser Pro Ile
1               5                   10

<210> SEQ ID NO 48
<211> LENGTH: 10
<212> TYPE: PRT
<213> ORGANISM: Artificial Sequence
<220> FEATURE:
<223> OTHER INFORMATION: peptide sequence

<400> SEQUENCE: 48

Gly Ala Glu Thr Phe Tyr Val Asp Gly Ala
1               5                   10

<210> SEQ ID NO 49
<211> LENGTH: 10
<212> TYPE: PRT
<213> ORGANISM: Artificial Sequence
<220> FEATURE:

<223> OTHER INFORMATION: peptide sequence

<400> SEQUENCE: 49

Ile Arg Lys Val Leu Phe Leu Asp Gly Ile
1               5                   10

<210> SEQ ID NO 50
<211> LENGTH: 10
<212> TYPE: PRT
<213> ORGANISM: Artificial Sequence
<220> FEATURE:
<223> OTHER INFORMATION: peptide sequence

<400> SEQUENCE: 50

Pro Asp Cys Ala Trp Leu Glu Ala Gln Glu
1               5                   10

<210> SEQ ID NO 51
<211> LENGTH: 8
<212> TYPE: PRT
<213> ORGANISM: Artificial Sequence
<220> FEATURE:
<223> OTHER INFORMATION: peptide sequence

<400> SEQUENCE: 51

Thr Gln Ile Met Phe Glu Thr Phe
1               5

<210> SEQ ID NO 52
<211> LENGTH: 8
<212> TYPE: PRT
<213> ORGANISM: Artificial Sequence
<220> FEATURE:
<223> OTHER INFORMATION: peptide sequence

<400> SEQUENCE: 52

Gly Gln Val Asn Tyr Glu Glu Phe
1               5

<210> SEQ ID NO 53
<211> LENGTH: 8
<212> TYPE: PRT
<213> ORGANISM: Artificial Sequence
<220> FEATURE:
<223> OTHER INFORMATION: peptide sequence

<400> SEQUENCE: 53

Pro Phe Ile Phe Glu Glu Glu Pro
1               5

<210> SEQ ID NO 54
<211> LENGTH: 8
<212> TYPE: PRT
<213> ORGANISM: Artificial Sequence
<220> FEATURE:
<223> OTHER INFORMATION: peptide sequence

<400> SEQUENCE: 54

Ser Phe Asn Phe Pro Gln Ile Thr
1               5

<210> SEQ ID NO 55
<211> LENGTH: 8
<212> TYPE: PRT
<213> ORGANISM: Artificial Sequence
<220> FEATURE:
<223> OTHER INFORMATION: peptide sequence

```
<400> SEQUENCE: 55

Asp Thr Val Leu Glu Glu Met Ser
1               5

<210> SEQ ID NO 56
<211> LENGTH: 8
<212> TYPE: PRT
<213> ORGANISM: Artificial Sequence
<220> FEATURE:
<223> OTHER INFORMATION: peptide sequence

<400> SEQUENCE: 56

Ala Arg Val Leu Ala Glu Ala Met
1               5

<210> SEQ ID NO 57
<211> LENGTH: 8
<212> TYPE: PRT
<213> ORGANISM: Artificial Sequence
<220> FEATURE:
<223> OTHER INFORMATION: peptide sequence

<400> SEQUENCE: 57

Ala Glu Glu Leu Ala Glu Ile Phe
1               5

<210> SEQ ID NO 58
<211> LENGTH: 8
<212> TYPE: PRT
<213> ORGANISM: Artificial Sequence
<220> FEATURE:
<223> OTHER INFORMATION: peptide sequence

<400> SEQUENCE: 58

Ser Leu Asn Leu Arg Glu Thr Asn
1               5

<210> SEQ ID NO 59
<211> LENGTH: 8
<212> TYPE: PRT
<213> ORGANISM: Artificial Sequence
<220> FEATURE:
<223> OTHER INFORMATION: peptide sequence

<400> SEQUENCE: 59

Ala Thr Ile Met Met Gln Arg Gly
1               5

<210> SEQ ID NO 60
<211> LENGTH: 8
<212> TYPE: PRT
<213> ORGANISM: Artificial Sequence
<220> FEATURE:
<223> OTHER INFORMATION: peptide sequence

<400> SEQUENCE: 60

Ala Glu Cys Phe Arg Ile Phe Asp
1               5

<210> SEQ ID NO 61
<211> LENGTH: 8
<212> TYPE: PRT
<213> ORGANISM: Artificial Sequence
<220> FEATURE:
<223> OTHER INFORMATION: peptide sequence
```

```
<400> SEQUENCE: 61

Asp Gln Ile Leu Ile Glu Ile Cys
1               5

<210> SEQ ID NO 62
<211> LENGTH: 8
<212> TYPE: PRT
<213> ORGANISM: Artificial Sequence
<220> FEATURE:
<223> OTHER INFORMATION: peptide sequence

<400> SEQUENCE: 62

Asp Asp Leu Phe Phe Glu Ala Asp
1               5

<210> SEQ ID NO 63
<211> LENGTH: 8
<212> TYPE: PRT
<213> ORGANISM: Artificial Sequence
<220> FEATURE:
<223> OTHER INFORMATION: peptide sequence

<400> SEQUENCE: 63

Tyr Glu Glu Phe Val Gln Met Met
1               5

<210> SEQ ID NO 64
<211> LENGTH: 8
<212> TYPE: PRT
<213> ORGANISM: Artificial Sequence
<220> FEATURE:
<223> OTHER INFORMATION: peptide sequence

<400> SEQUENCE: 64

Pro Ile Val Gly Ala Glu Thr Phe
1               5

<210> SEQ ID NO 65
<211> LENGTH: 8
<212> TYPE: PRT
<213> ORGANISM: Artificial Sequence
<220> FEATURE:
<223> OTHER INFORMATION: peptide sequence

<400> SEQUENCE: 65

Thr Leu Asn Phe Pro Ile Ser Pro
1               5

<210> SEQ ID NO 66
<211> LENGTH: 8
<212> TYPE: PRT
<213> ORGANISM: Artificial Sequence
<220> FEATURE:
<223> OTHER INFORMATION: peptide sequence

<400> SEQUENCE: 66

Arg Glu Ala Phe Arg Val Phe Asp
1               5

<210> SEQ ID NO 67
<211> LENGTH: 8
<212> TYPE: PRT
<213> ORGANISM: Artificial Sequence
<220> FEATURE:
<223> OTHER INFORMATION: peptide sequence

<400> SEQUENCE: 67
```

```
Ala Glu Thr Phe Tyr Val Asp Lys
1               5

<210> SEQ ID NO 68
<211> LENGTH: 8
<212> TYPE: PRT
<213> ORGANISM: Artificial Sequence
<220> FEATURE:
<223> OTHER INFORMATION: peptide sequence

<400> SEQUENCE: 68

Ala Gln Thr Phe Tyr Val Asn Leu
1               5

<210> SEQ ID NO 69
<211> LENGTH: 8
<212> TYPE: PRT
<213> ORGANISM: Artificial Sequence
<220> FEATURE:
<223> OTHER INFORMATION: peptide sequence

<400> SEQUENCE: 69

Pro Thr Leu Leu Thr Glu Ala Pro
1               5

<210> SEQ ID NO 70
<211> LENGTH: 8
<212> TYPE: PRT
<213> ORGANISM: Artificial Sequence
<220> FEATURE:
<223> OTHER INFORMATION: peptide sequence

<400> SEQUENCE: 70

Ser Phe Ile Gly Met Glu Ser Ala
1               5

<210> SEQ ID NO 71
<211> LENGTH: 8
<212> TYPE: PRT
<213> ORGANISM: Artificial Sequence
<220> FEATURE:
<223> OTHER INFORMATION: peptide sequence

<400> SEQUENCE: 71

Asp Ala Ile Asn Thr Glu Phe Lys
1               5

<210> SEQ ID NO 72
<211> LENGTH: 8
<212> TYPE: PRT
<213> ORGANISM: Artificial Sequence
<220> FEATURE:
<223> OTHER INFORMATION: peptide sequence

<400> SEQUENCE: 72

Gln Ile Thr Leu Trp Gln Arg Pro
1               5

<210> SEQ ID NO 73
<211> LENGTH: 8
<212> TYPE: PRT
<213> ORGANISM: Artificial Sequence
<220> FEATURE:
<223> OTHER INFORMATION: peptide sequence

<400> SEQUENCE: 73
```

```
Glu Leu Glu Phe Pro Glu Gly Gly
1               5

<210> SEQ ID NO 74
<211> LENGTH: 7
<212> TYPE: PRT
<213> ORGANISM: Artificial Sequence
<220> FEATURE:
<223> OTHER INFORMATION: peptide sequence

<400> SEQUENCE: 74

Ala Asn Leu Ala Glu Glu Ala
1               5

<210> SEQ ID NO 75
<211> LENGTH: 8
<212> TYPE: PRT
<213> ORGANISM: Artificial Sequence
<220> FEATURE:
<223> OTHER INFORMATION: peptide sequence

<400> SEQUENCE: 75

Ser Gln Asn Tyr Pro Ile Val Gln
1               5

<210> SEQ ID NO 76
<211> LENGTH: 8
<212> TYPE: PRT
<213> ORGANISM: Artificial Sequence
<220> FEATURE:
<223> OTHER INFORMATION: peptide sequence

<400> SEQUENCE: 76

Pro Gly Asn Phe Leu Gln Ser Arg
1               5

<210> SEQ ID NO 77
<211> LENGTH: 7
<212> TYPE: PRT
<213> ORGANISM: Artificial Sequence
<220> FEATURE:
<223> OTHER INFORMATION: peptide sequence

<400> SEQUENCE: 77

Lys Leu Val Phe Phe Ala Glu
1               5

<210> SEQ ID NO 78
<211> LENGTH: 8
<212> TYPE: PRT
<213> ORGANISM: Artificial Sequence
<220> FEATURE:
<223> OTHER INFORMATION: peptide sequence

<400> SEQUENCE: 78

Gly Asp Ala Leu Leu Glu Arg Asn
1               5

<210> SEQ ID NO 79
<211> LENGTH: 8
<212> TYPE: PRT
<213> ORGANISM: Artificial Sequence
<220> FEATURE:
<223> OTHER INFORMATION: peptide sequence

<400> SEQUENCE: 79

Lys Glu Leu Tyr Pro Leu Thr Ser
```

```
<210> SEQ ID NO 80
<211> LENGTH: 8
<212> TYPE: PRT
<213> ORGANISM: Artificial Sequence
<220> FEATURE:
<223> OTHER INFORMATION: peptide sequence

<400> SEQUENCE: 80

Arg Gln Ala Asn Phe Leu Gly Lys
1               5

<210> SEQ ID NO 81
<211> LENGTH: 8
<212> TYPE: PRT
<213> ORGANISM: Artificial Sequence
<220> FEATURE:
<223> OTHER INFORMATION: peptide sequence

<400> SEQUENCE: 81

Ser Arg Ser Leu Tyr Ala Ser Ser
1               5

<210> SEQ ID NO 82
<211> LENGTH: 8
<212> TYPE: PRT
<213> ORGANISM: Artificial Sequence
<220> FEATURE:
<223> OTHER INFORMATION: peptide sequence

<400> SEQUENCE: 82

Ala Glu Ala Met Ser Gln Val Thr
1               5

<210> SEQ ID NO 83
<211> LENGTH: 8
<212> TYPE: PRT
<213> ORGANISM: Artificial Sequence
<220> FEATURE:
<223> OTHER INFORMATION: peptide sequence

<400> SEQUENCE: 83

Arg Lys Ile Leu Phe Leu Asp Gly
1               5

<210> SEQ ID NO 84
<211> LENGTH: 8
<212> TYPE: PRT
<213> ORGANISM: Artificial Sequence
<220> FEATURE:
<223> OTHER INFORMATION: peptide sequence

<400> SEQUENCE: 84

Gly Ser His Leu Val Glu Ala Leu
1               5

<210> SEQ ID NO 85
<211> LENGTH: 8
<212> TYPE: PRT
<213> ORGANISM: Artificial Sequence
<220> FEATURE:
<223> OTHER INFORMATION: peptide sequence

<400> SEQUENCE: 85

Gly Gly Val Tyr Ala Thr Arg Ser
1               5
```

<210> SEQ ID NO 86
<211> LENGTH: 8
<212> TYPE: PRT
<213> ORGANISM: Artificial Sequence
<220> FEATURE:
<223> OTHER INFORMATION: peptide sequence

<400> SEQUENCE: 86

Phe Arg Ser Gly Val Glu Thr Thr
1               5

<210> SEQ ID NO 87
<211> LENGTH: 8
<212> TYPE: PRT
<213> ORGANISM: Artificial Sequence
<220> FEATURE:
<223> OTHER INFORMATION: peptide sequence

<400> SEQUENCE: 87

Val Glu Val Ala Glu Glu Glu Glu
1               5

<210> SEQ ID NO 88
<211> LENGTH: 8
<212> TYPE: PRT
<213> ORGANISM: Artificial Sequence
<220> FEATURE:
<223> OTHER INFORMATION: peptide sequence

<400> SEQUENCE: 88

Leu Pro Val Asn Gly Glu Phe Ser
1               5

<210> SEQ ID NO 89
<211> LENGTH: 8
<212> TYPE: PRT
<213> ORGANISM: Artificial Sequence
<220> FEATURE:
<223> OTHER INFORMATION: peptide sequence

<400> SEQUENCE: 89

Glu Thr Thr Ala Leu Val Cys Asp
1               5

<210> SEQ ID NO 90
<211> LENGTH: 8
<212> TYPE: PRT
<213> ORGANISM: Artificial Sequence
<220> FEATURE:
<223> OTHER INFORMATION: peptide sequence

<400> SEQUENCE: 90

His Leu Val Glu Ala Leu Tyr Leu
1               5

<210> SEQ ID NO 91
<211> LENGTH: 8
<212> TYPE: PRT
<213> ORGANISM: Artificial Sequence
<220> FEATURE:
<223> OTHER INFORMATION: peptide sequence

<400> SEQUENCE: 91

His Tyr Gly Phe Pro Thr Tyr Gly
1               5

<210> SEQ ID NO 92
<211> LENGTH: 8
<212> TYPE: PRT
<213> ORGANISM: Artificial Sequence
<220> FEATURE:
<223> OTHER INFORMATION: peptide sequence

<400> SEQUENCE: 92

Asp Ser Ala Asp Ala Glu Glu Asp
1               5

<210> SEQ ID NO 93
<211> LENGTH: 8
<212> TYPE: PRT
<213> ORGANISM: Artificial Sequence
<220> FEATURE:
<223> OTHER INFORMATION: peptide sequence

<400> SEQUENCE: 93

Gly Trp Ile Leu Gly Glu His Gly
1               5

<210> SEQ ID NO 94
<211> LENGTH: 8
<212> TYPE: PRT
<213> ORGANISM: Artificial Sequence
<220> FEATURE:
<223> OTHER INFORMATION: peptide sequence

<400> SEQUENCE: 94

Gly Trp Ile Leu Ala Glu His Gly
1               5

<210> SEQ ID NO 95
<211> LENGTH: 7
<212> TYPE: PRT
<213> ORGANISM: Artificial Sequence
<220> FEATURE:
<223> OTHER INFORMATION: peptide sequence

<400> SEQUENCE: 95

Ala Ile Tyr Leu Ala Leu Gln
1               5

<210> SEQ ID NO 96
<211> LENGTH: 8
<212> TYPE: PRT
<213> ORGANISM: Artificial Sequence
<220> FEATURE:
<223> OTHER INFORMATION: peptide sequence

<400> SEQUENCE: 96

Glu Lys Val Tyr Leu Ala Trp Val
1               5

<210> SEQ ID NO 97
<211> LENGTH: 8
<212> TYPE: PRT
<213> ORGANISM: Artificial Sequence
<220> FEATURE:
<223> OTHER INFORMATION: peptide sequence

<400> SEQUENCE: 97

Val Glu Ile Cys Thr Glu Met Glu
1               5

```
<210> SEQ ID NO 98
<211> LENGTH: 8
<212> TYPE: PRT
<213> ORGANISM: Artificial Sequence
<220> FEATURE:
<223> OTHER INFORMATION: peptide sequence

<400> SEQUENCE: 98

Thr Gln Asp Phe Trp Glu Val Gln
1               5

<210> SEQ ID NO 99
<211> LENGTH: 8
<212> TYPE: PRT
<213> ORGANISM: Artificial Sequence
<220> FEATURE:
<223> OTHER INFORMATION: peptide sequence

<400> SEQUENCE: 99

Leu Trp Met Gly Tyr Glu Leu His
1               5

<210> SEQ ID NO 100
<211> LENGTH: 8
<212> TYPE: PRT
<213> ORGANISM: Artificial Sequence
<220> FEATURE:
<223> OTHER INFORMATION: peptide sequence

<400> SEQUENCE: 100

Gly Asp Ala Tyr Phe Ser Val Pro
1               5

<210> SEQ ID NO 101
<211> LENGTH: 8
<212> TYPE: PRT
<213> ORGANISM: Artificial Sequence
<220> FEATURE:
<223> OTHER INFORMATION: peptide sequence

<400> SEQUENCE: 101

Glu Leu Glu Leu Ala Glu Asn Arg
1               5

<210> SEQ ID NO 102
<211> LENGTH: 8
<212> TYPE: PRT
<213> ORGANISM: Artificial Sequence
<220> FEATURE:
<223> OTHER INFORMATION: peptide sequence

<400> SEQUENCE: 102

Ser Lys Asp Leu Ile Ala Glu Ile
1               5

<210> SEQ ID NO 103
<211> LENGTH: 8
<212> TYPE: PRT
<213> ORGANISM: Artificial Sequence
<220> FEATURE:
<223> OTHER INFORMATION: peptide sequence

<400> SEQUENCE: 103

Leu Glu Val Asn Ile Val Thr Asp
1               5

<210> SEQ ID NO 104
```

```
<211> LENGTH: 8
<212> TYPE: PRT
<213> ORGANISM: Artificial Sequence
<220> FEATURE:
<223> OTHER INFORMATION: peptide sequence

<400> SEQUENCE: 104

Gly Gly Asn Tyr Pro Val Gln His
1               5

<210> SEQ ID NO 105
<211> LENGTH: 8
<212> TYPE: PRT
<213> ORGANISM: Artificial Sequence
<220> FEATURE:
<223> OTHER INFORMATION: peptide sequence

<400> SEQUENCE: 105

Ala Arg Leu Met Ala Glu Ala Leu
1               5

<210> SEQ ID NO 106
<211> LENGTH: 8
<212> TYPE: PRT
<213> ORGANISM: Artificial Sequence
<220> FEATURE:
<223> OTHER INFORMATION: peptide sequence

<400> SEQUENCE: 106

Pro Phe Ala Ala Ala Gln Gln Arg
1               5

<210> SEQ ID NO 107
<211> LENGTH: 8
<212> TYPE: PRT
<213> ORGANISM: Artificial Sequence
<220> FEATURE:
<223> OTHER INFORMATION: peptide sequence

<400> SEQUENCE: 107

Pro Arg Asn Phe Pro Val Ala Gln
1               5

<210> SEQ ID NO 108
<211> LENGTH: 8
<212> TYPE: PRT
<213> ORGANISM: Artificial Sequence
<220> FEATURE:
<223> OTHER INFORMATION: peptide sequence

<400> SEQUENCE: 108

Gly Leu Ala Ala Pro Gln Phe Ser
1               5

<210> SEQ ID NO 109
<211> LENGTH: 8
<212> TYPE: PRT
<213> ORGANISM: Artificial Sequence
<220> FEATURE:
<223> OTHER INFORMATION: peptide sequence

<400> SEQUENCE: 109

Ser Leu Asn Leu Pro Val Ala Lys
1               5

<210> SEQ ID NO 110
<211> LENGTH: 8
```

<212> TYPE: PRT
<213> ORGANISM: Artificial Sequence
<220> FEATURE:
<223> OTHER INFORMATION: peptide sequence

<400> SEQUENCE: 110

Ala Glu Thr Phe Tyr Thr Asp Gly
1               5

<210> SEQ ID NO 111
<211> LENGTH: 8
<212> TYPE: PRT
<213> ORGANISM: Artificial Sequence
<220> FEATURE:
<223> OTHER INFORMATION: peptide sequence

<400> SEQUENCE: 111

Arg Gln Val Leu Phe Leu Glu Lys
1               5

<210> SEQ ID NO 112
<211> LENGTH: 9
<212> TYPE: PRT
<213> ORGANISM: Artificial Sequence
<220> FEATURE:
<223> OTHER INFORMATION: peptide sequence

<400> SEQUENCE: 112

Gln Met Ile Phe Lys Glu Glu His Gly
1               5

<210> SEQ ID NO 113
<211> LENGTH: 8
<212> TYPE: PRT
<213> ORGANISM: Artificial Sequence
<220> FEATURE:
<223> OTHER INFORMATION: peptide sequence

<400> SEQUENCE: 113

Ser Gln Asn Tyr Pro Ile Val Gln
1               5

<210> SEQ ID NO 114
<211> LENGTH: 8
<212> TYPE: PRT
<213> ORGANISM: Artificial Sequence
<220> FEATURE:
<223> OTHER INFORMATION: peptide sequence

<400> SEQUENCE: 114

Glu Glu Glu Leu Ala Glu Cys Phe
1               5

<210> SEQ ID NO 115
<211> LENGTH: 8
<212> TYPE: PRT
<213> ORGANISM: Artificial Sequence
<220> FEATURE:
<223> OTHER INFORMATION: peptide sequence

<400> SEQUENCE: 115

Thr Gln Ile Met Phe Glu Thr Phe
1               5

<210> SEQ ID NO 116
<211> LENGTH: 8
<212> TYPE: PRT

```
<213> ORGANISM: Artificial Sequence
<220> FEATURE:
<223> OTHER INFORMATION: peptide sequence

<400> SEQUENCE: 116

Gly Gln Val Asn Tyr Glu Glu Phe
1               5

<210> SEQ ID NO 117
<211> LENGTH: 8
<212> TYPE: PRT
<213> ORGANISM: Artificial Sequence
<220> FEATURE:
<223> OTHER INFORMATION: peptide sequence

<400> SEQUENCE: 117

Gly Cys Asn Tyr Pro Val Gln His
1               5

<210> SEQ ID NO 118
<211> LENGTH: 8
<212> TYPE: PRT
<213> ORGANISM: Artificial Sequence
<220> FEATURE:
<223> OTHER INFORMATION: peptide sequence

<400> SEQUENCE: 118

Pro Arg Asn Phe Pro Val Ala Gln
1               5

<210> SEQ ID NO 119
<211> LENGTH: 8
<212> TYPE: PRT
<213> ORGANISM: Artificial Sequence
<220> FEATURE:
<223> OTHER INFORMATION: peptide sequence

<400> SEQUENCE: 119

Ala Glu Glu Leu Ala Glu Ile Phe
1               5

<210> SEQ ID NO 120
<211> LENGTH: 8
<212> TYPE: PRT
<213> ORGANISM: Artificial Sequence
<220> FEATURE:
<223> OTHER INFORMATION: peptide sequence

<400> SEQUENCE: 120

Pro Phe Ala Ala Ala Gln Gln Arg
1               5

<210> SEQ ID NO 121
<211> LENGTH: 8
<212> TYPE: PRT
<213> ORGANISM: Artificial Sequence
<220> FEATURE:
<223> OTHER INFORMATION: peptide sequence

<400> SEQUENCE: 121

Arg Gln Val Leu Phe Leu Glu Lys
1               5

<210> SEQ ID NO 122
<211> LENGTH: 8
<212> TYPE: PRT
<213> ORGANISM: Artificial Sequence
```

```
<220> FEATURE:
<223> OTHER INFORMATION: peptide sequence

<400> SEQUENCE: 122

Ala Thr Ile Met Met Gln Arg Gly
1               5

<210> SEQ ID NO 123
<211> LENGTH: 8
<212> TYPE: PRT
<213> ORGANISM: Artificial Sequence
<220> FEATURE:
<223> OTHER INFORMATION: peptide sequence

<400> SEQUENCE: 123

Ser Leu Asn Leu Pro Val Ala Lys
1               5

<210> SEQ ID NO 124
<211> LENGTH: 7
<212> TYPE: PRT
<213> ORGANISM: Artificial Sequence
<220> FEATURE:
<223> OTHER INFORMATION: peptide sequence

<400> SEQUENCE: 124

Ala Asn Leu Ala Glu Glu Ala
1               5

<210> SEQ ID NO 125
<211> LENGTH: 8
<212> TYPE: PRT
<213> ORGANISM: Artificial Sequence
<220> FEATURE:
<223> OTHER INFORMATION: peptide sequence

<400> SEQUENCE: 125

Pro Thr Leu Leu Thr Glu Ala Pro
1               5

<210> SEQ ID NO 126
<211> LENGTH: 8
<212> TYPE: PRT
<213> ORGANISM: Artificial Sequence
<220> FEATURE:
<223> OTHER INFORMATION: peptide sequence

<400> SEQUENCE: 126

Ser Phe Ile Gly Met Glu Ser Ala
1               5

<210> SEQ ID NO 127
<211> LENGTH: 8
<212> TYPE: PRT
<213> ORGANISM: Artificial Sequence
<220> FEATURE:
<223> OTHER INFORMATION: peptide sequence

<400> SEQUENCE: 127

Tyr Glu Glu Phe Val Gln Met Met
1               5

<210> SEQ ID NO 128
<211> LENGTH: 8
<212> TYPE: PRT
<213> ORGANISM: Artificial Sequence
<220> FEATURE:
```

```
<223> OTHER INFORMATION: peptide sequence

<400> SEQUENCE: 128

Arg His Val Met Thr Asn Leu Gly
1               5

<210> SEQ ID NO 129
<211> LENGTH: 8
<212> TYPE: PRT
<213> ORGANISM: Artificial Sequence
<220> FEATURE:
<223> OTHER INFORMATION: peptide sequence

<400> SEQUENCE: 129

Tyr Ile Ser Ala Ala Glu Leu Arg
1               5

<210> SEQ ID NO 130
<211> LENGTH: 8
<212> TYPE: PRT
<213> ORGANISM: Artificial Sequence
<220> FEATURE:
<223> OTHER INFORMATION: peptide sequence

<400> SEQUENCE: 130

Gly Leu Ala Ala Pro Gln Phe Ser
1               5

<210> SEQ ID NO 131
<211> LENGTH: 8
<212> TYPE: PRT
<213> ORGANISM: Artificial Sequence
<220> FEATURE:
<223> OTHER INFORMATION: peptide sequence

<400> SEQUENCE: 131

Asp Gly Asn Gly Thr Ile Asp Phe
1               5

<210> SEQ ID NO 132
<211> LENGTH: 8
<212> TYPE: PRT
<213> ORGANISM: Artificial Sequence
<220> FEATURE:
<223> OTHER INFORMATION: peptide sequence

<400> SEQUENCE: 132

Gly Asp Ala Leu Leu Glu Arg Asn
1               5

<210> SEQ ID NO 133
<211> LENGTH: 8
<212> TYPE: PRT
<213> ORGANISM: Artificial Sequence
<220> FEATURE:
<223> OTHER INFORMATION: peptide sequence

<400> SEQUENCE: 133

Asn Pro Thr Glu Ala Glu Leu Gln
1               5

<210> SEQ ID NO 134
<211> LENGTH: 8
<212> TYPE: PRT
<213> ORGANISM: Artificial Sequence
<220> FEATURE:
<223> OTHER INFORMATION: peptide sequence
```

```
<400> SEQUENCE: 134

Arg Gln Ala Gly Phe Leu Gly Leu
1               5

<210> SEQ ID NO 135
<211> LENGTH: 13
<212> TYPE: PRT
<213> ORGANISM: Artificial Sequence
<220> FEATURE:
<223> OTHER INFORMATION: peptide sequence

<400> SEQUENCE: 135

Ser Ser Arg Lys Arg Arg Ser His Asp Val Leu Thr Gln
1               5                   10

<210> SEQ ID NO 136
<211> LENGTH: 13
<212> TYPE: PRT
<213> ORGANISM: Artificial Sequence
<220> FEATURE:
<223> OTHER INFORMATION: peptide sequence

<400> SEQUENCE: 136

Arg Ile Phe Gly Arg Arg Ser Ile Pro Val Asn Glu Gln
1               5                   10

<210> SEQ ID NO 137
<211> LENGTH: 13
<212> TYPE: PRT
<213> ORGANISM: Artificial Sequence
<220> FEATURE:
<223> OTHER INFORMATION: peptide sequence

<400> SEQUENCE: 137

Val Arg Gly Ala Arg Arg Ser Gly Asp Val Leu Trp Gln
1               5                   10

<210> SEQ ID NO 138
<211> LENGTH: 13
<212> TYPE: PRT
<213> ORGANISM: Artificial Sequence
<220> FEATURE:
<223> OTHER INFORMATION: peptide sequence

<400> SEQUENCE: 138

Ser Ala Ala Gln Arg Arg Gly Arg Ile Gly Arg Asn Gln
1               5                   10

<210> SEQ ID NO 139
<211> LENGTH: 13
<212> TYPE: PRT
<213> ORGANISM: Artificial Sequence
<220> FEATURE:
<223> OTHER INFORMATION: peptide sequence

<400> SEQUENCE: 139

Phe Ala Glu Gly Arg Arg Gly Ala Ala Glu Val Leu Gln
1               5                   10

<210> SEQ ID NO 140
<211> LENGTH: 13
<212> TYPE: PRT
<213> ORGANISM: Artificial Sequence
<220> FEATURE:
<223> OTHER INFORMATION: peptide sequence
```

```
<400> SEQUENCE: 140

Lys Leu Ala Gln Arg Arg Val Phe His Gly Val Ala Gln
1               5                   10

<210> SEQ ID NO 141
<211> LENGTH: 13
<212> TYPE: PRT
<213> ORGANISM: Artificial Sequence
<220> FEATURE:
<223> OTHER INFORMATION: peptide sequence

<400> SEQUENCE: 141

Met Lys Thr Gly Arg Arg Gly Ser Ala Asn Gly Lys Gln
1               5                   10

<210> SEQ ID NO 142
<211> LENGTH: 9
<212> TYPE: PRT
<213> ORGANISM: Artificial Sequence
<220> FEATURE:
<223> OTHER INFORMATION: peptide sequence

<400> SEQUENCE: 142

Val Ser Gln Asn Tyr Ile Val Gln Asn
1               5
```